United States Patent
Sheppard et al.

(10) Patent No.: US 10,087,252 B2
(45) Date of Patent: Oct. 2, 2018

(54) METHODS AND COMPOSITIONS FOR TREATING AND PREVENTING DISEASE ASSOCIATED WITH αVβ5 INTEGRIN

(75) Inventors: Dean Sheppard, Oakland, CA (US);
George Su, San Francisco, CA (US);
Amha Atakilit, Oakland, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 401 days.

(21) Appl. No.: 13/386,323

(22) PCT Filed: Jul. 26, 2010

(86) PCT No.: PCT/US2010/043211
§ 371 (c)(1),
(2), (4) Date: Aug. 29, 2012

(87) PCT Pub. No.: WO2011/011775
PCT Pub. Date: Jan. 27, 2011

(65) Prior Publication Data
US 2012/0328604 A1    Dec. 27, 2012

Related U.S. Application Data

(60) Provisional application No. 61/228,416, filed on Jul. 24, 2009.

(51) Int. Cl.
*A61K 39/395* (2006.01)
*C07K 16/28* (2006.01)
*A61K 39/00* (2006.01)

(52) U.S. Cl.
CPC ...... *C07K 16/2839* (2013.01); *C07K 16/2848* (2013.01); *A61K 2039/505* (2013.01); *C07K 2317/76* (2013.01)

(58) Field of Classification Search
None
See application file for complete search history.

(56) References Cited

U.S. PATENT DOCUMENTS

| | | |
|---|---|---|
| 4,816,567 A | 3/1989 | Cabilly et al. |
| 5,519,138 A | 5/1996 | Ries et al. |
| 5,527,679 A | 6/1996 | Hemler et al. |
| 5,530,101 A | 6/1996 | Queen et al. |
| 5,585,089 A | 12/1996 | Queen et al. |
| 5,693,761 A | 12/1997 | Queen et al. |
| 5,693,762 A | 12/1997 | Queen et al. |
| 5,777,085 A | 7/1998 | Co et al. |
| 5,780,426 A | 7/1998 | Palladino et al. |
| 5,859,205 A | 1/1999 | Adair et al. |
| 6,069,158 A | 5/2000 | Miller et al. |
| 6,180,370 B1 | 1/2001 | Queen et al. |
| 6,210,671 B1 | 4/2001 | Co |
| 6,291,196 B1 | 9/2001 | Vielkind |
| 6,329,511 B1 | 12/2001 | Vasquez et al. |
| 6,683,051 B1 | 1/2004 | Jonczyk et al. |
| 6,692,741 B2 | 2/2004 | Huang et al. |
| 7,053,041 B1 | 5/2006 | Brooks et al. |
| 7,815,908 B2 * | 10/2010 | Sheppard et al. ......... 424/143.1 |
| 2002/0004042 A1 | 1/2002 | Factor |
| 2002/0037889 A1 | 3/2002 | Duggan et al. |
| 2002/0072500 A1 | 6/2002 | Rogers et al. |
| 2002/0077321 A1 | 6/2002 | Khanna et al. |
| 2003/0139398 A1 | 7/2003 | Hoekstra et al. |
| 2003/0171271 A1 | 9/2003 | Baciu et al. |
| 2003/0181440 A1 | 9/2003 | Costanzo et al. |
| 2004/0010023 A1 | 1/2004 | Stahle et al. |
| 2004/0018192 A1 | 1/2004 | Wakabayashi et al. |
| 2004/0019035 A1 | 1/2004 | Patane |
| 2004/0019037 A1 | 1/2004 | Askew et al. |
| 2004/0019206 A1 | 1/2004 | Ruminiski et al. |
| 2005/0226865 A1 * | 10/2005 | Sheppard et al. ......... 424/141.1 |
| 2007/0128203 A1 | 6/2007 | Giles-Komar et al. |
| 2012/0129757 A1 * | 5/2012 | Li ...................... A61K 38/1709 514/1.1 |
| 2016/0017041 A1 * | 1/2016 | Violette ............ A61K 39/3955 424/133.1 |
| 2017/0362324 A1 * | 12/2017 | Cameron ........... C07K 16/2839 |

FOREIGN PATENT DOCUMENTS

| | | |
|---|---|---|
| DE | 4142366 | 6/1993 |
| EP | 0173494 A3 | 8/1985 |
| JP | 2008-512462 A | 4/2008 |
| WO | 87/02671 | 5/1987 |
| WO | 90/07861 | 7/1990 |
| WO | 98/14192 | 4/1998 |

(Continued)

OTHER PUBLICATIONS

Ganter et al. Role of Small GTPases and avb5 Integrin in Pseudomonas aeruginosa—Induced Increase in Lung Endothelial Permeability. Am J Respir Cell Mol Biol vol. 40. pp. 108-118, 2009 Published online on Aug. 14, 2008.*
Leroy-Dudal et al. Role of avb5 integrins and vitronectin in Pseudomonas aeruginosa PAK interaction with A549 respiratory cells. Microbes and Infection 6 (2004) 875-881.*
Lange et al. Assessment of vascular permeability in an ovine model of acute lung injury and pneumonia-induced Pseudomonas aeruginosa sepsis. Crit Care Med 2008; 36:1284-1289.*
Seok et al. Genomic responses in mouse models poorly mimic human inflammatory diseases. PNAS | Feb. 26, 2013 | vol. 110 | No. 9 | 3507-3512.*
Su et al. Genetic Deficiency and Antibody Blockade of Integrin Avb5 Decreases Lung and Systemic Vascular Permeability, Acute Lung Injury, and Sepsis Mortality. American Thoracic Society International Conference Abstracts, A61. Lung Endothelium Functions: The Barrier and Beyond. Am J respir Cric Care Med 182:2011:A1950. Absract 1950, 2011.*

(Continued)

*Primary Examiner* — Maher M Haddad
(74) *Attorney, Agent, or Firm* — Kilpatrick, Townsend & Stockton LLP

(57) ABSTRACT

The present invention provides compositions and methods for treating and preventing disease associated with αvβ5 integrin by blocking binding to αvβ5 integrin. In particular, antibodies specific for αvβ5 integrin are useful for preventing, treating, and reversing sepsis.

12 Claims, 5 Drawing Sheets

(56) References Cited

FOREIGN PATENT DOCUMENTS

| WO | 98/30542 | 7/1998 |
|---|---|---|
| WO | 99/07405 | 2/1999 |
| WO | 02/12501 | 2/2002 |
| WO | 04/020435 | 3/2004 |
| WO | 2005/094391 A2 | 10/2005 |
| WO | WO 2006/029167 A2 | 3/2006 |
| WO | WO 2006/029167 A3 | 3/2006 |

OTHER PUBLICATIONS

Al-Lazikani et al.,"Standard Conformations for the Canonical Structures of Immunoglobulins", *Journal of Molecular Biology* 273:927-948, 1997.

Baluk et al., "Neurogenic plasma leakage in mouse airways", *British Journal of Pharmacology* 126:522-528, 1999.

Bernard et al., "The American-European Consensus Conference on ARDS", *American Journal of Respiratory and Critical Care Medicine* 149:818-824, 1994.

Burvenich et al., "Monoclonal antibody 14C5 targets integrin αvβ5." *Molecular Cancer Therapeutics* 3771-3779, 2008.

Chothia et al., "Canonical Structures for the Hypervariable Regions of Immunoglobulins", *Journal of Molecular Biology* 196:901-917, 1987.

Chothia et al., "Conformations of immunoglobulin hypervariable regions", *Nature* 342:877-883, 1989.

Chothia et al., "Structural Repertoire of the Human VH Segments", *Journal of Molecular Biology* 227:799-817, 1992.

Cordeiro, F., "Technology evaluation: Lerdelimumab, Cambridge Antibody Technology", *Current Opinion in Molecular Therapeutics* 5(2):199-203, 2003.

Crawford et al., "Thrombospondin-1 Is a Major Activator of TGF-β1 In Vivo", *Cell* 93:1159-1170, 1998.

Dacosta et al., "SB-505124 Is a Selective Inhibitor of Transforming Growth Factor-β Type I Receptors ALK4, ALK5, and ALK7", *Molecular Pharmacology* 65(3):744-52, 2004.

Depaola et al., "Electrical Impedance of Cultured Endothelium Under Fluid Flow", *Annals of Biomedical Engineering* 29:648-656, 2001.

European Search report dated Jan. 13, 2013 for European Application No. 10803008.1, 7 pages.

Ferring et al., "Is outcome from ARDS related to the severity of respiratory failure?", *European Respiratory Journal* 10:1297-1300, 1997.

Groeneveld, J., "Vascular pharmacology of acute lung injury and acute respiratory distress syndrome", *Vascular Pharmacology* 39:247-256, 2003.

Hotchkiss et al., "The Pathophysiology and Treatment of Sepsis", *The New England Journal of Medicine* 348:138-150, 2003.

Iskander et al., "Cecal Ligation and Puncture-Induced Murine Sepsis Does Not Cause Lung Injury*." *Critical Care Medicine* 41(1):159-170, 2013.

Jones et al., "Replacing the complementarity-determining regions in a human antibody with those from a mouse", *Nature* 321:522-535, 1986.

Laping, N., "ALK5 inhibition in renal disease", *Current Opinion in Pharmacology* 3:204-208, 2003.

Laping et al., "Inhibition of Transforming Growth Factor (TGF)-β1-Induced Extracellular Matrix with a Novel Inhibitor of the TGF-β Type I Receptor Kinase Activity: SB-431542", *Molecular Pharmacology* 62(1):58-64, 2002.

Lefranc, M., "IMGT, The international ImMunoGeneTics database", *Nucleic Acids Research* 29(1):207-209, 2001.

Ling et al., "Therapeutic Role of TGF-β-Neutralizing Antibody in Mouse Cyclosporin A Nephropathy: Morphologic Improvement Associated with Functional Preservation", *Journal of the American Society of Nephrology* 14:377-388, 2003.

MacCallum et al., "Antibody-antigen Interactions: Contact Analysis and Binding Site Topography", *Journal of Molecular Biology* 262:732-745, 1996.

Martin et al., "Modeling antibody hypervariable loops: A Combined algorithm", *Proceedings of the National Academy of Sciences USA* 86:9268-9272, 1989.

Martin et al., "Molecular Modeling of Antibody Combining Sites", *Methods in Enzymology* 203:121-153, 1991.

McCaffree et al., "Role of pulmonary edema in the acute pulmonary response to sepsis", *Journal of Applied Physiology Respiratory Environmental and Exercise Physiology* 50(6):1198-1205, 1981.

McCormick et al., "Anti-TGF-β Treatment Prevents Skin and Lung Fibrosis in Murine Sclerodermatous Graft-Versus-Host Disease: A Model for Human Scleroderma", *The Journal of Immunology* 163:5693-5699, 1999.

Michel, C., "The Transport of Albumin: A Critique of the Vesicular System in Transendothelial Transport", *American Review of Respiratory Disease* 146:S32-S36, 1992.

Morrison et al., "Genetically Engineered Antibody Molecules", *Advances in Immunology* 44:65-92, 1988.

Morrison et al., "Chimeric human antibody molecules: Mouse antigen-binding domains with human constant region domains", *Proceedings of the National Academy of Sciences USA* 81:6851-6855, 1984.

Office Action dated Apr. 25, 2013 for Chinese Application 201080033367.3, English Translation, 10 pages.

Padlan, E., "A possible procedure for reducing the immunogenicity of antibody variable domains while preserving their ligand-binding properties", *Molecular Immunology* 28(4/5):489-498, 1991.

Padlan, E., "Anatomy of the antibody molecule", *Molecular Immunology* 31(3):169-217, 1994.

Pedersen et al., "Antibody Modeling: Beyond Homology", *Immunomethods*, 1:126-136, 1992.

Pittet et al., "TGF-β is a critical mediator of acute lung injury", *The Journal of Clinical Investigation* 107:1537-1544, 2001.

Rees et al., "Antibody combining sites: structure and prediction", In Sternberg M.J.E. (ed.), *Protein Structure Prediction*. Oxford University Press, Oxford, 141-172, 1996.

Renkin, E., "Capillary transport of macromolecules: pores and other endothelial pathways", *Journal of Applied Physiology* 58:315-325, 1985.

Ribeiro et al., "The Activation Sequence of Thrombospondin-1 Interacts with the Latency-associated Peptide to Regulate Activation of Latent Transforming Growth Factor-β*", *The Journal of Biological Chemistry* 58:315-325, 1985.

Rittirsch et al., "Immunodesign of experimental sepsis by cecal ligation and puncture", *Nature Protocols* 4(1):31-36, 2008.

Ruiz et al., "IMGT, the international ImMunoGeneTics database", *Nucleic Acids Research* 28(1): 219-221, 2000.

Schultz-Cherry et al., "Thrombospondin Binds and Activates the Small and Large Forms of Latent Transforming Growth Factor-β in a Chemically Defined System", *The Journal of Biological Chemistry* 269(43):26775-26782, 1994.

Seker et al., "Expression of Integrins in Cerebral Arteriovenous and Cavernous Malformations", *Neurosurgery* 58(1):159-168, 2006.

Stupack et al., "Apoptosis of adherent cells by recruitment of caspase-8 to unligated integrins.", *The Journal of Cell Biology* 155(3):459-470, 2001.

Su et al., "Absence of Integrin αvβ3 Enhances Vascular Leak in Mice by Inhibiting Endothelial Cortical Actin Formation.", *American Journal of Respiratory and Critical Care Medicine* 185(1):58-66, 2012.

Su et al., "Effective Treatment of Mouse Sepsis With an Inhibitory Antibody Targeting Integrin αvβ3*." *Critical Care Medicine* 41(2):546-553, 2013.

Varner et al., "Integrin α5β1 Expression Negatively Regulates Cell Growth: Reversal by Attachment to Fibronectin.", *The American Society for Cell Biology* 6:725-740, 1995.

Verhoeyen et al., "Reshaping Human Antibodies: Grafting an Antilysozyme Activity", *Science*, 239:1534-1536, 1988.

(56) References Cited

OTHER PUBLICATIONS

Wang et al., "Effects of Delayed Treatment with Transforming Growth Factor-β Soluble Receptor in a Three-dose Bleomycin Model of Lung Fibrosis in Hamsters", *Experimental Lung Research* 28:405-417, 2002.
Wang et al., "Reduction of bleomycin induced lung fibrosis by transforming growth factor β soluble receptor in hamsters", *Thorax* 54:805-812, 1999.
Winter et al., "Man-made antibodies", *Nature* 349:293-299, 1991.
Yao et al., "Identification and characterization of nonsedimentable lipid-protein microvesicles", *Proceedings of the National Academy of Sciences USA* 88:2269-2273, 1991.
Zhang et al. "Latency-Associated Peptide Prevents Skin Fibrosis in Murine Sclerodermatous Graft-Versus-Host Disease, a Model for Human Scleroderma", *The Journal of Investigative Dermatology* 121(4):713-719, 2003.
Branch, A.D., "A good antisense molecule is hard to find," Feb. 1998, Trends Biochem Sci., 23(2):45-50.
Brooks et al. "Insulin-like Growth Factor Receptor Cooperates With Integrin αvβ5 to Promote Tumor Cell Dissemination In Vivo." J. Clin. Invest. (Mar. 1997), 99(6):1390-1398.
Chorev et al. "Approach to Discovering Novel Therapeutic Agents for Osteoporosis Based on Integrin Receptor Blockade." Biopolymers (1995), 37:367-375.
Elicieri et al. "Src-mediated coupling of focal adhesion kinase to integrin αvβ5 in vascular endothelial growth factor signaling." J. Cell Biol. (Apr. 2002), 157(1):149-159.
European Search Report dated Aug. 13, 2008 for European Patent Application No. 05763460.2, 4 pages.
European Search dated Jan. 25, 2012 Report for European Application No. 11180077.7, 10 pages.
Friedlander et al. "Definition of Two Angiogenic Pathways by Distinct $\alpha_v$ Integrins." Science (Dec. 1995), 270(5241):1500-1502.
Friedlander et al. "Involvement of integrins $\alpha_v\beta_5$ in ocular neovascular diseases." Proc. Natl. Acad. Sci. USA (Sep. 1996), 93(18):9764-9769.
Goodman et al. "Nanomolar Small Molecule Inhibitors for αvβ6, αvβ6, and αvβ3 Integrins." J. Med Chem. (2002), 45(5):1045-1051.
Heba et al. "The Time Course of Tumor Necrosis Factor-α, Inducible Nitric Oxide Synthase and Vascular Endothelial Growth Factor Expression in an Experimental Model of Chronic Myocardial Infarction in Rats." J. Vasc. Res. (2001), 38(3):288-300.
Huang, Xiaozhu et al.; "Normal Development, Wound Healing, and Adenovirus Susceptibility in β5-Deficient Mice"; 2000, Molecular and Cellular Biology, vol. 20, No. 3, pp. 755-759.
Huang, Z., "Structural chemistry and therapeutic intervention of protein-protein interactions in immune response, human immunodeficiency virus entry, and apoptosis," Jun. 2000, Pharmacol Ther., 86(3), 2001-215.
Hynes, Richard O. "Integrins: Versatility, Modulation, and Signaling in Cell Adhesion." Cell (Apr. 1992), 69:11-25.
International Preliminary Report on Patentability and Written Opinion dated Sep. 14, 2010 for International Application No. PCT/US2010/43211, 5 pages.
International Preliminary Report on Patentability and Written Opinion dated Apr. 24, 2006 for International Application No. PCT/US2005/11222, 3 pages.
International Search Report dated Oct. 24, 2005 for International Application No. PCT/US2005/11222, 1 page.
International Search Report dated Sep. 14, 2010 for International Application No. PCT/US2010/43211, 2 pages.
Kakouros et al. "Non-Cardiogenic Pulmonary Edema." Hellenic J. Cardiol. (2003), 44:385-391.

Li et al. "VEGF, flk-1, and flt-1 expression in a rat myocardial infarction model of angiogenesis." Am. J. Physiol. (1996), 270(5 Pt 2):H1803-H1811.
Meerovtich, Karen et al., "A novel RGD antagonist that targets both αvβ3 and α5β1 includes apoptosis of angiogenic endothelial cells on type I collagen", Vascular Pharmacology 40:77-89, 2003.
Mountain, A., "Gene therapy: the first decade." Mar., 2000, Trends Biotechnology 18(3):119-128.
Pasqualini et al. "A Peptide Isolated from Phage Display Libraries Is a Structural and Functional Mimic of an RGD-binding Site on Integrins." J. Cell. Biol. (Sep. 1995), 130(5):1189-1196.
Pasqualini et al. "A study of the structure, function and distribution of $\beta_5$ integrins using novel anti-$\beta_5$ monoclonal antibodies." J. Cell Science (1993), 105:101-111.
Pasqualini et al. "Contrasting Roles for Integrin $\beta_1$ and $\beta_5$ Cytoplasmic Domains in Subcellular Localization, Cell Proliferation, and Cell Migration." J. Cell Biology (Apr. 1994), 125(2):447-460.
Pierschbacher et al. "Manipulation of Cellular Interactions With Biomaterials Toward a Therapeutic Outcome: A Perspective." J. Cell Biochem. (1994), 56:150-154.
Ruoslahti, E. "RGD and Other Recognition Sequences for Integrins." Ann. Rev. Cell. Dev. Biol. (1996), 12:697-715.
Smith et al. "Building Synthetic Antibodies as Adhesive Ligands for Integrins." J. Biol. Chem. (Dec. 1994), 269(52):32788-32795.
Soeki et al. "Serial Changes in Serum VEGF and HGF in Patients with Acute Myocardial Infarction." Cardiology (2000), 93(3):168-174.
Su et al., "Integrin αvβ5 regulates lung vascular permeability and pulmonary endothelial barrier function", Am. J. Respir. Cell Mol. Biol 2007 36(3):377-386.
Tabata et al., "Induction of an epithelial integrin alphavbeta6 in human cytomegalovirus-infected endothelial cells leads to activation of transforming growth factor-beta1 and increased collagen production", Amer. J. Pathol ePub Apr. 2008 172:1127-1140, especially p. 1128 right col. paragraph 2.
Thickett, Dave R. et al., "Vascular endothelial growth factor may contribute to increased vascular permeability in acute respiratory distress syndrome", American Journal of Respiratory and Critical Care Medicine 164:1601-1605, 2001.
Toole et al., Storming Media: the role of EMMPRIN in Tumor angiogenesis and metastasis, abstract, May 2001.
Wang et al., "A single amino acid determines lysophospholipid specifically of the S1P1 (EDG1) and LPA1 (EDG2) phospholipid growth factor receptors," Dec. 2001, J. Biol. Chem. 276(52): 49213-49220.
Wayner et al. "Integrins αvβ3 and αvβ5 Contribute to Cell Attachment to Vitronectin but Differentially Distribute on the Cell Surface." J. Cell Biol. (May 1991), 113(4):919-929.
Japanese Office Action dated Jul. 28, 2014 for Japanese Patent Application No. 2012-521872, 7 pages. (English Translation).
Arribas et al., "A Probiotic Strain of *Escherichia coil*, Nissle 1917, Given Orally Exerts Local and Systemic Anti-Inflammatory Effects in Lipopolysaccharide-induced Sepsis in Mice," *British Journal of Pharmacology* (2009), 157, 1024-1033.
Hu et al., "The Role of Hepatic Invariant NKT Cells in Systemic/Local Inflammation and Mortality During Polymicrobial Septic Shock," *The Journal of Immunology* (2009), 2467-2475.
Martin, et al., "Approach to the Patient with Sepsis," *Clin Chest Med*. 30 (2009), 1-16.
Micek, et al. "Pseudomonas aeruginosa bloodstream infection: importance of appropriate initial antimicrobial treatment." Antimicrobial agents and chemotherapy 49, No. 4 (2005): 1306-1311.
Summons to Attend Oral Proceedings in EP10803008.1, dated Apr. 13, 2018, 10 pages.

\* cited by examiner

METHODS AND COMPOSITIONS FOR TREATING AND PREVENTING DISEASE ASSOCIATED WITH αVβ5 INTEGRIN

CROSS-REFERENCES TO RELATED APPLICATIONS

This present application is a U.S. National Phase Application under 35 U.S.C. § 371 of International Application No. PCT/US2010/043211, filed Jul. 26, 2010, which claims the benefit of U.S. Provisional Application No. 61/228,416, filed Jul. 24, 2009, all of which are expressly incorporated herein by reference in their entireties and for all purposes.

STATEMENT AS TO RIGHTS TO INVENTIONS MADE UNDER FEDERALLY SPONSORED RESEARCH AND DEVELOPMENT

This work was supported in part by NIH Ro1 HL083950 "Regulation of vascular permeability by integrin αvβ5." The government has certain rights in the invention.

BACKGROUND OF THE INVENTION

Sepsis syndrome results from an exaggerated cascade of inflammation initiated by complex interactions between an infectious organism and host immune, inflammatory, and coagulation responses (Hotchkiss and Karl (2003) *N Engl J Med* 348:138). Inflammatory agonists elevated during sepsis, including TNF-α and thrombin, increase permeability in endothelial monolayers. Increased systemic vascular permeability leads to redistribution of fluid and solutes to extravascular compartments, resulting in hypovolemia, hemoconcentration, and hemostasis.

Over 650,000 cases of sepsis are diagnosed a year with 20 to 50 percent mortality, making sepsis the most common cause of death among hospitalized patients in non-coronary intensive care units. Though it is generally accepted that host response (involving multiple cell types, inflammatory mediators, and coagulation factors) determines sepsis-associated mortality, clinical trials have largely failed to identify effective therapeutic targets. Molecular mechanisms underlying the development and maintenance of sepsis remain poorly understood and effective pharmacologic targets for these severe disease syndromes have not been identified.

As indicated above, sepsis is characterized by increased vascular permeability in response to an exaggerated inflammatory cascade. Solutes pass through an endothelial barrier via paracellular pathways or through receptor-mediated transcytosis (Michel (1992) *Am Rev Respir Dis* 146:S32; Renkin (1985) *J Appl Physiol* 58:315). Current general consensus is that paracellular pathways are primarily responsible for the increased vascular permeability seen in acute inflammatory disease states (Groeneveld (2002) *Vascul Pharmacol* 39:247; Bernard et al. (1994) *Am J Respir Crit. Care Med* 149:818). One frequently cited model suggests that paracellular gaps form due to imbalanced competition between cytoskeletal, adhesive cell-cell, and cell-matrix forces. In this model, cytoskeletal filamentous (F)-actin polymerizes into morphologically distinct stress fibers which transmit actomyosin-generated tension between cell junctions and focal adhesions. Focal adhesions (FA) are large macromolecular assemblies that link the actin cytoskeleton to the extracellular matrix (ECM) and localize signaling proteins to sites of integrin binding and clustering.

The present disclosure reveals integrins αvβ5 and αvβ3 as important regulators of endothelial barrier function in response to inflammatory agonists. Surprisingly, these closely related integrins support opposing cellular mechanisms that lead to differential organization of permeability-inducing (αvβ5 and actin stress fibers) and barrier-enhancing (αvβ3 and cortical actin) cytoskeletal structures. We report here the unexpectedly distinct roles of integrins αvβ5 and Δvβ3 in the regulation of vascular permeability in sepsis.

BRIEF SUMMARY OF THE INVENTION

The present invention provides compositions and methods for treating or preventing diseases involving αvβ5 integrin such as sepsis.

In some embodiments, the invention provides methods of treating, reversing, or preventing sepsis in a mammalian subject (e.g., a primate such as a human, a monkey, or a chimpanzee; canine; feline; or livestock animal, such as a horse, bovine, or sheep). A therapeutic amount or prophylactic amount of an antagonist of αvβ5 integrin is administered to the subject.

In some embodiments, the antagonist is an agent that inhibits the activity or expression of αvβ5 integrin. In some embodiments, the agent is selected from a αvβ5 specific antibody, a small molecule inhibitor of αvβ5 integrin, or a polynucleotide inhibitor of αvβ5 integrin, such as an antisense molecule. In some embodiments, the agent does not inhibit the activity or expression of at least one of Δvβ3, β3, αvβ6, β6, αvβ8, or β8.

In some embodiments, the antagonist is an antibody or an antibody fragment, e.g., a chimeric or humanized antibody, scFv, Fab, or (Fab')2. In some embodiments, the antibody does not significantly bind to, or block ligand binding to, αvβ3 integrin. In some embodiments, the antibody does not significantly bind to at least one of αvβ3, β3, αvβ6, β6, αvβ8, or β8. In some embodiments, the antibody does not significantly bind to αvβ3, β3, αvβ6, β6, αvβ8, or β8.

In some embodiments, the antibody specifically competes for specific binding to αvβ5 integrin with ALULA (the antibody produced by the hybridoma deposited under ATCC Deposit No. PTA-5817). In some embodiments, the antibody binds to the same epitope of αvβ5 integrin as ALULA. In some embodiments, the antibody is derived from the CDRs of ALULA and has substantially similar CDR amino acid sequences (e.g., 90, 95, 97, 98, 99, or 100% identity over the CDRs of ALULA). In some embodiments, the antibody comprises V regions that are substantially similar to the amino acid sequences of the ALULA V regions (e.g., 90, 95, 96, 97, 98, 99, or 100% identity over the V regions of ALULA). The antibody can be ALULA itself, humanized ALULA, chimeric ALULA, a fragment of ALULA including, e.g., a scFv, a Fab, and a (Fab')₂ of ALULA, or another antibody that competes with ALULA for binding to αvβ5 integrin.

In some embodiments, the method comprises administration of a pharmaceutical composition comprising an antibody specific for αvβ5 integrin, and not administering an antibody or antagonist that binds to αvβ3 integrin.

The methods of the invention are useful for treating individuals that have sepsis or are at risk of developing sepsis. Administration can be, but is not limited to, intravenous, or intraperitoneal. The administration can be a monotherapy or, as with typical practice, in conjunction with other therapeutics intended to treat or prevent complications associated with sepsis, e.g., intravenous fluids, pressors, surgical intervention, antibiotics, activated protein C, insulin, GM-CSF, a TGFβ pathway inhibitor, a β-2 agonist, a diuretic agent, an antagonist of αvβ5 integrin, a second antibody that specifically binds to αvβ5 integrin, an antagonist of αvβ6 integrin, vasoconstrictors and inotropic drugs (e.g., phenylephrine, norepinephrine, dopamine, dobutamine).

A further embodiment of the invention provides methods of identifying an agent for treating sepsis. In some embodiments, the methods comprise contacting a plurality of agents with αvβ5 integrin, selecting an agent that competes with binding of a ligand to αvβ5 integrin, and determining the effect of the selected agent on sepsis. In some embodiments, the methods comprise contacting a plurality of agents with αvβ5 integrin, selecting an agent that competes for αvβ5 binding with ALULA, and determining the effect of the selected agent on sepsis. In some embodiments, the methods further comprises a step of eliminating agents that bind to αvβ3. In some embodiments, the antibody does not significantly bind to αvβ3, β3, αvβ6, β6, αvβ8, or β8. Agents which have an effect on sepsis are identified as agents for treating sepsis. The plurality of agents may be a plurality of antibodies. The ligand may be an antibody, including, e.g., ALULA, or may be vitronectin, fibronectin, osteopontin, tenascin c, or an adenovirus penton base.

These and other embodiments of the invention are further illustrated by the detailed description that follows.

DETAILED DESCRIPTION OF THE INVENTION

I. Introduction

Figure 1:
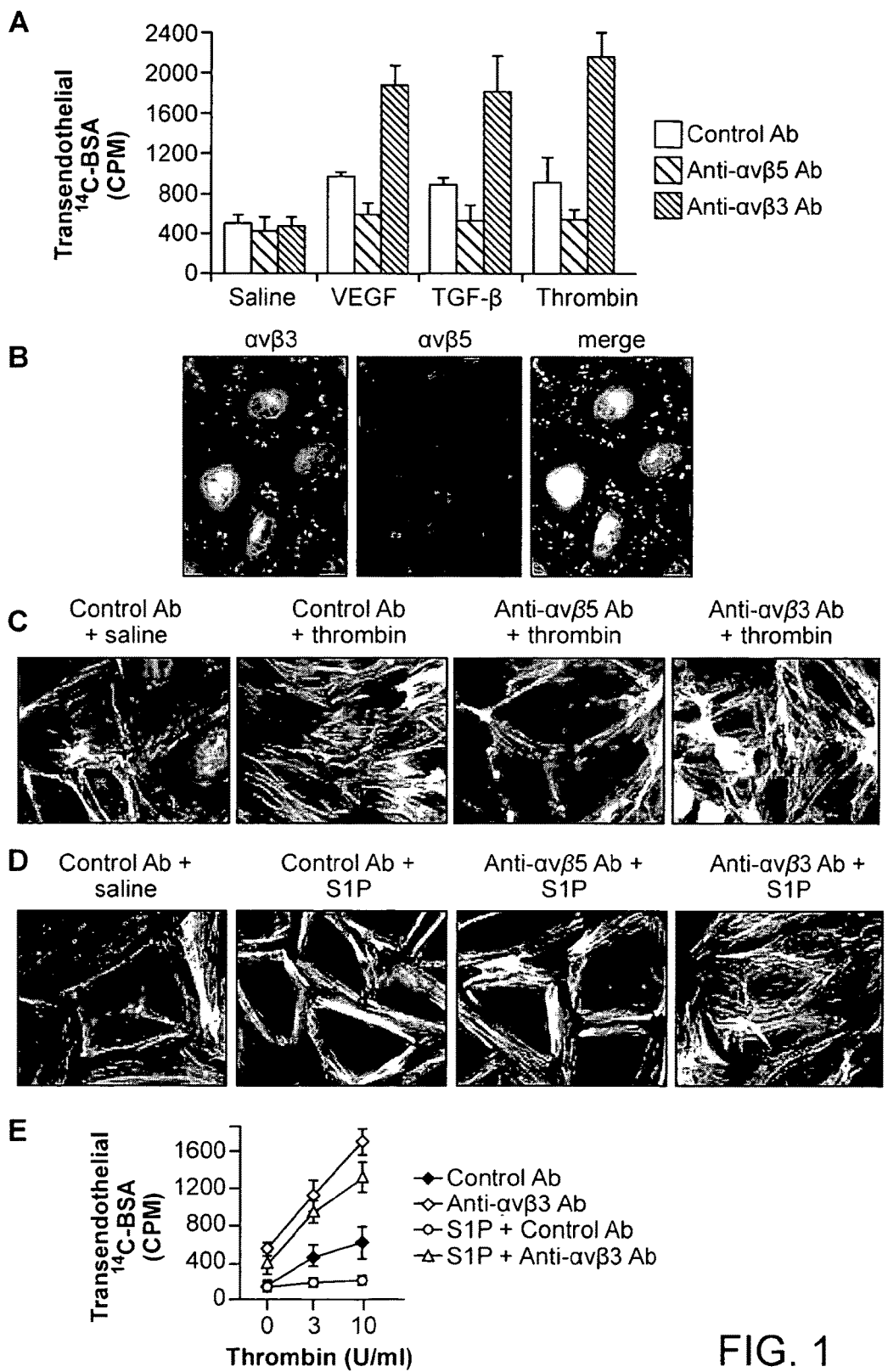
FIG. 1A: Agonist-induced permeability in human pulmonary artery endothelial cells (HPAECs) is attenuated by antibody inhibition of αvβ5 and enhanced by antibody inhibition of αvβ3. Serum-starved confluent HPAEC monolayers on Transwells® were incubated with αvβ3 and αvβ5 antibodies (anti-αvβ3 and αvβ5 Ab) (10 µg/ml) or control (10 µg/ml) antibodies (Ab) 1 hour before stimulation with VEGF (30 ng/ml), TGF-β (10 ng/ml), or thrombin (10 U/ml). Transendothelial leak was determined by application of a $C^{14}$-albumin tracer to the apical well and subsequent collection and scintillation counting (counts per minute) (CPM) of basolateral well contents after 1 hour. Data shown are the means+/−standard errors, n=3.
FIG. 1B: αvβ3 and αvβ5 co-localize at focal adhesions. Confluent monolayers of HPAECs were fixed, permeabilized, and stained with αvβ3- and αvβ5-specific (followed by Alex 488-labeled and rhodamine-labeled secondary antibodies). Integrins αvβ3 and αvβ5 were pseudocolored green and red, respectively, and merged using Image Pro® software.
FIGS. 1C and D: αvβ5 preferentially supports thrombin-induced stress fiber formation and αvβ3 preferentially supports S1P-induced cortical actin formation. Confluent monolayers of HPAECs were pretreated with either isotype control (Control Ab), αvβ3, or αvβ5 antibodies (10 µg/ml) for one hour, then stimulated with thrombin (10 U/ml for 10 minutes) or S1P (0.5 µM for 10 minutes). Cells were then fixed, permeabilized, and stained with rhodamine-phalloidin.
FIG. 1E: αvβ3 blockade overcomes S1P protection against thrombin-induced permeability. Serum-starved confluent HPAEC monolayers on Transwells® were incubated with αvβ3 or isotype control antibodies (10 µg/ml) and/or S1P (0.5 µM) 1 hour before stimulation with thrombin. Transendothelial leak was determined by application of a $C^{14}$-albumin tracer to the apical well and subsequent collection and scintillation counting (counts per minute) (CPM) of basolateral well contents after 1 hour. Data shown are the means+/−standard errors, n=3.

The present invention is based in part on the surprising discovery that treating animals with agents that bind to αvβ5 integrins reduces symptoms of sepsis. The inventors have demonstrated that an antibody that binds to αvβ5 integrin blocks ligand binding to αvβ5 integrin. More particularly, blocking binding of αvβ5 integrin can reduce the severity of sepsis. The present results are striking because the administration of αvβ5 blocking antibodies actually reverses sepsis. Standard sepsis therapeutics generally seek to prevent sepsis, e.g., by use of antibiotics or anti-inflammatory agents. Usually, the acute nature of the septic reaction requires immediate and aggressive medical intervention; standard therapeutics are not effective. Accordingly, the invention provides methods of treating, preventing, or reversing sepsis in a subject by administering an effective amount of an antagonist of αvβ5 to the subject.

The invention also provides methods of identifying new agents for the treatment of sepsis by identifying agents that interact with αvβ5 integrins and testing them for their ability to treat sepsis.

II. Definitions

An "αvβ5 Antagonist" is any Agent that Competes with an αvβ5 Ligand for Available ligand binding sites on αvβ5 integrins. αvβ5 antagonists include agents that specifically bind to αvβ5 or β5, or that can inhibit the activity or expression of αvβ5 integrin. Examples include antibodies, small molecule inhibitors, and polynucleotide inhibitors (e.g., antisense and siRNA).

An "αvβ5 integrin" is a member of a family of adhesion molecules that comprise non-covalently associated α/β heterodimers that mediate, inter alia, cell-cell interactions, cell-extracellular matrix (ECM) interactions, and cell-pathogen interactions. αvβ5 is the only integrin that contains the β5 subunit. αvβ5 recognizes the RGD peptide sequence and binds vitronectin (see, e.g., Hynes, *Cell* 69:11-25 (1992) and has been implicated in multiple disorders including stroke, myocardial infarction, cancer (i.e., angiogenesis), and ocular neovascularization disease (see, e.g., Friedlander et al., *Science* 270(5241):1500-2 (1995); Friedlander et al., *PNAS USA* 93(18):9764-9 (1996); Elicieri et al., *J. Cell Biol.* 157(10:149-159 (2002); Heba et al., *J. Vasc. Res.* 38(3):288-300 (2001); Soeki et al., *Cardiology* 93(3):168-74 (2000); and Li et al., *Am. J. Physiol.* 270(5 Pt 2):H1803-11 (1996). αv and β5 have both been sequenced and characterized (see, e.g., Hynes, 1992 supra, and U.S. Pat. No. 5,527,679, respectively). The activities of αvβ5 integrin thus include, but are not limited to, RGD and vitronectin binding and mediating cell-cell, cell-ECM, and cell-pathogen interactions.

Sepsis is characterized by evidence of acute inflammation present throughout the body, e.g., fever and abnormal white blood cell count. Sepsis is sometimes caused by bacterial infection, thus, symptoms of the bacterial infection itself may also be indicative. Accordingly, an individual at risk of sepsis can include one that is suffering from an infection, in particular a severe infection, or one that has experienced sepsis in the past.

In the septic reaction, the immune system reacts to the infection and can cause tissue damage and changes to metabolism. Outward physical symptoms of this response frequently include a high heart rate (above 90 beats per minute), high respiratory rate (above 20 breaths per minute), elevated white blood cell (WBC) count (above 12,000) and elevated or lowered body temperature (under 36° C. or over 38° C.). The immunological response causes widespread activation of acute phase proteins which then cause damage to the vasculature and organs. Extreme cases result in death. As with any disease or disorder, one of skill in medicine can best recognize and diagnose sepsis. One of skill will also recognize that "sepsis" is not an absolute term, but can be used to refer to systemic inflammatory response syndrome, severe sepsis, and septic shock.

A "therapeutic dose," "therapeutic amount," "therapeutically effective amount," or "effective amount" of an αvβ5 integrin antagonist is an amount of the antagonist which prevents, alleviates, abates, or reduces the severity of symptoms of diseases associated with αvβ5 integrin including, e.g., sepsis in a patient.

As used herein, the terms "treat" and "prevent" are not intended to be absolute terms. Treatment can refer to any delay in onset, amelioration of symptoms, improvement in patient survival, reduction of tissue damage, etc. Indeed, in some embodiments, treatment according to the invention can result in reversal of the disease. Similarly, prevention can refer to any delay in onset or, depending on context, reduction in severity of symptoms. The effect of treatment can be compared to an individual or pool of individuals not receiving the treatment, or to the same patient, e.g., before treatment.

The term "subject" is used broadly herein to refer to any individual that is considered for treatment. Typically, the subject is a human or some other mammal.

The term "antibody" refers to a polypeptide encoded by an immunoglobulin gene or functional fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms "variable heavy chain," "$V_H$," or "VH" refer to the variable region of an immunoglobulin heavy chain, including an Fv, scFv, dsFv or Fab; while the terms "variable light chain," "$V_L$" or "VL" refer to the variable region of an immunoglobulin light chain, including of an Fv, scFv, dsFv or Fab.

Examples of antibody functional fragments include, but are not limited to, complete antibody molecules, antibody fragments, such as Fv, single chain Fv (scFv), complementarity determining regions (CDRs), VL (light chain variable region), VH (heavy chain variable region), Fab, F(ab)$_2$' and any combination of those or any other functional portion of an immunoglobulin peptide capable of binding to target antigen (see, e.g., FUNDAMENTAL IMMUNOLOGY (Paul ed., 4th ed. 2001). As appreciated by one of skill in the art, various antibody fragments can be obtained by a variety of methods, for example, digestion of an intact antibody with an enzyme, such as pepsin; or de novo synthesis. Antibody fragments are often synthesized de novo either chemically or by using recombinant DNA methodology. Thus, the term antibody, as used herein, includes antibody fragments either produced by the modification of whole antibodies, or those synthesized de novo using recombinant DNA methodologies (e.g., single chain Fv) or those identified using phage display libraries (see, e.g., McCafferty et al., (1990) *Nature* 348:552). The term "antibody" also includes bivalent or bispecific molecules, diabodies, triabodies, and tetrabodies. Bivalent and bispecific molecules are described in, e.g., Kostelny et al. (1992) *J. Immunol.* 148:1547, Pack and Pluckthun (1992) *Biochemistry* 31:1579, Hollinger et al. (1993), *PNAS. USA* 90:6444, Gruber et al. (1994) *J. Immunol.* 152:5368, Zhu et al. (1997) *Protein Sci.* 6:781, Hu et al. (1996) *Cancer Res.* 56:3055, Adams et al. (1993) *Cancer Res.* 53:4026, and McCartney, et al. (1995) *Protein Eng.* 8:301.

"Single chain Fv (scFv)" or "single chain antibodies" refers to a protein wherein the $V_H$ and the $V_L$ regions of a scFv antibody comprise a single chain which is folded to create an antigen binding site similar to that found in two chain antibodies. Methods of making scFv antibodies have been described in e.g., Ward et al., *Exp Hematol.* (5):660-4 (1993); and Vaughan et al., *Nat. Biotechnol.* 14(3):309-14 (1996). Single chain Fv (scFv) antibodies optionally include a peptide linker of no more than 50 amino acids, generally no more than 40 amino acids, preferably no more than 30 amino acids, and more preferably no more than 20 amino acids in length. In some embodiments, the peptide linker is a concatamer of the sequence Gly-Gly-Gly-Gly-Ser, e.g., 2, 3, 4, 5, or 6 such sequences. However, it is to be appreciated that some amino acid substitutions within the linker can be made. For example, a valine can be substituted for a glycine. Additional peptide linkers and their use are well-known in the art. See, e.g., Huston et al., *Proc. Nat'l Acad. Sci. USA* 8:5879 (1988); Bird et al., *Science* 242:4236 (1988); Glockshuber et al., *Biochemistry* 29:1362 (1990); U.S. Pat. No. 4,946,778, U.S. Pat. No. 5,132,405 and Stemmer et al., *Biotechniques* 14:256-265 (1993).

As used herein, "chimeric antibody" refers to an immunoglobulin molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region, or portion thereof, having a different or altered antigen specificity; or with corresponding sequences from another species or from another antibody class or subclass.

As used herein, "humanized antibody" refers to an immunoglobulin molecule in which CDRs from a donor antibody are grafted onto human framework sequences. Humanized antibodies may also comprise residues of donor origin in the framework sequences. The humanized antibody can also comprise at least a portion of a human immunoglobulin constant region. Humanized antibodies may also comprise residues which are found neither in the recipient antibody nor in the imported CDR or framework sequences. Humanization can be performed using methods known in the art (e.g., Jones et al., Nature 321:522-525; 1986; Riechmann et al., Nature 332:323-327, 1988; Verhoeyen et al., *Science* 239:1534-1536, 1988); Presta, *Curr. Op. Struct. Biol.* 2:593-596, 1992; U.S. Pat. No. 4,816,567), including techniques such as "superhumanizing" antibodies (Tan et al., *J. Immunol.* 169: 1119, 2002) and "resurfacing" (e.g., Staelens et al., *Mol. Immunol.* 43: 1243, 2006; and Roguska et al., *Proc. Natl. Acad. Sci. USA* 91: 969, 1994).

As used herein, "V-region" refers to an antibody variable region domain comprising the segments of Framework 1 (F1), Complementarity Detemlining Region 1 (CDR1), F2, CDR2, and F3, including CDR3 and F4, which segments are added to the V-segment as a consequence of rearrangement of the heavy chain and light chain V-region genes during B-cell differentiation. A "V-segment" as used herein refers to the region of the V-region (heavy or light chain) that is encoded by a V gene. The V-segment of the heavy chain variable region encodes FR1-CDR1-FR2-CDR2 and FR3. For the purposes of this invention, the V-segment of the light chain variable region is defined as extending though FR3 up to CDR3.

As used herein, the term "J-segment" refers to a subsequence of the variable region encoded comprising a C-terminal portion of a CDR3 and the FR4. An endogenous J-segment is encoded by an immunoglobulin J-gene.

As used herein, "complementarity-determining region (CDR)" refers to one of the three hypervariable regions in each chain that interrupt the four "framework" regions established by the light and heavy chain variable regions. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, for example, a $V_H$ CDR3 is located in the variable domain of the heavy chain of the antibody in which it is found, whereas a $V_L$ CDR1 is the CDR1 from the variable domain of the light chain of the antibody in which it is found.

The sequences of the framework regions of different light or heavy chains are relatively conserved within a species. The framework region of an antibody, that is the combined framework regions of the constituent light and heavy chains, serves to position and align the CDRs in three dimensional space. Thus, the position of the CDRs within the V region is relatively conserved between antibodies.

The amino acid sequences and positions of the CDRs and framework regions can be determined using various well known definitions in the art, e.g., Kabat, Chothia, international ImMunoGeneTics database (IMGT), and AbM (see, e.g., Johnson et al., supra; Chothia & Lesk, 1987, Canonical structures for the hypervariable regions of immunoglobulins. *J. Mol. Biol.* 196, 901-917; Chothia C. et al., 1989, Conformations of immunoglobulin hypervariable regions. Nature 342, 877-883; Chothia C. et al., 1992, structural repertoire of the human VH segments J. Mol. Biol. 227, 799-817; Al-Lazikani et al., *J. Mol. Biol.* 1997, 273(4)). Definitions of antigen combining sites are also described in the following: Ruiz et al., IMGT, the international ImMunoGeneTics database. *Nucleic Acids Res.*, 28, 219-221 (2000); and Lefranc, M.-P. IMGT, the international ImMunoGeneTics database. *Nucleic Acids Res.* January 1; 29(1): 207-9 (2001); MacCallum et al, Antibody-antigen interactions: Contact analysis and binding site topography, *J. Mol. Biol.*, 262 (5), 732-745 (1996); and Martin et al, *Proc. Natl. Acad. Sci.* USA, 86, 9268-9272 (1989); Martin, et al, *Methods Enzymol.*, 203, 121-153, (1991); Pedersen et al, *Immunomethods*, 1, 126, (1992); and Rees et al, In Sternberg M. J. E. (ed.), Protein Structure Prediction. Oxford University Press, Oxford, 141-172 1996).

The phrase "specifically (or significantly or selectively) binds to" when referring to a given protein or peptide, refers to a binding reaction which is determinative of the presence of the protein in the presence of a heterogeneous population of proteins and other biologics. Thus, under designated immunoassay conditions, the specified antibodies bind to a particular protein (e.g., αvβ5 integrin, β5, or portions thereof) and do not bind in a significant amount to other proteins present in the sample. Specific binding to an antibody under such conditions may require an antibody that is selected for its specificity for a particular protein. For example, antibodies raised against an αvβ5 integrins or a β5 polypeptide can be further selected to obtain antibodies specifically immunoreactive with that protein and not with other proteins. In some embodiments, the specific antibody will also bind to polymorphic variants of the protein, e.g., proteins at least 80%, 85%, 90%, 95% or 99% identical to a sequence of interest. In some embodiments, the antibodies of the invention are selected to specifically bind to an epitope on αvβ5 or β5, without significant binding to αvβ3 or β3. In some embodiments, the αvβ5 specific antibody does not significantly bind to αvβ6, β6, β8, or αvβ8.

One of skill will understand that "specific" or "significant" binding are not intended to be absolute terms. For example, if an antibody does not significantly bind to a particular epitope, it binds with at least 5-fold, 8-fold, 10-fold, 20-fold, 50-fold, 80-fold, or 100-fold reduced affinity as compared to the epitope against which the antibody was raised. For example, an αvβ5-specific antibody does not significantly bind to αvβ3, αvβ6, or αvβ8 if it binds to the latter with less than 20%, 10%, 5%, 1%, 0.5%, 0.1%, 0.05%, 0.01% or less affinity than to αvβ5. Binding affinity can be determined using techniques known in the art, e.g., ELISAs. Affinity can be expressed as dissociation constant (Kd or $K_D$). A relatively higher Kd indicates lower affinity. Thus, for example, the Kd of an αvβ5-specific antibody for αvβ5 will typically be lower by a factor of at least 5, 8, 10, 15, 20, 50, 100, 500, 1000, or more than the Kd of the αvβ5-specific antibody with another protein. One of skill will understand how to design controls to indicate non-specific binding and compare relative binding levels.

A variety of immunoassay formats may be used to select antibodies specifically immunoreactive with a particular protein. For example, solid-phase ELISA immunoassays, Western blots, or immunohistochemistry are routinely used to select monoclonal antibodies specifically immunoreactive with a protein. See, Harlow and Lane *Antibodies, A Laboratory Manual*, Cold Spring Harbor Publications, NY (1988) for a description of immunoassay formats and conditions that can be used to determine specific immunoreactivity. Typically, a specific or selective reaction will be at least twice the background signal or noise and more typically more than 10 to 100 times background.

An agent that "specifically competes" for binding reduces the specific binding of an antibody to a polypeptide. A first antibody is considered to competitively inhibit binding of a second antibody, if binding of the second antibody to the antigen is reduced by at least 30%, usually at least about 40%, 50%, 60%, 75%, or at least about 90%, in the presence of the first antibody using any of the competitive binding assays known in the art (see, e.g., Harlow and Lane, supra).

The term "equilibrium dissociation constant" or "affinity" abbreviated (Kd or $K_D$), refers to the dissociation rate constant ($k_d$, time$^{-1}$) divided by the association rate constant ($k_a$, time$^{-1}$ M$^{-1}$). Equilibrium dissociation constants can be measured using any known method in the art. Antibodies with high affinity have a monovalent affinity less than about 10 nM, and often less than about 500 pM or about 50 pM as determined by surface plasmon resonance analysis performed at 37° C. In some embodiments, the antibodies of the invention have an affinity (as measured using surface plasmon resonance), of less than 500 pM, typically less than about 100 pM, or even less than 25 pM.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full length proteins (i.e., antigens), wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "peptidomimetic" and "mimetic" refer to a synthetic chemical compound that has substantially the same structural and functional characteristics of the αvβ5 antagonists of the invention. Peptide analogs are commonly used in the pharmaceutical industry as non-peptide drugs with properties analogous to those of the template peptide. These types of non-peptide compound are termed "peptide mimetics" or "peptidomimetics" (see, e.g., Fauchere, *J. Adv. Drug Res.* 15:29 (1986); Veber and Freidinger *TINS* p. 392 (1985); and Evans et al. *J. Med. Chem.* 30:1229 (1987)). Peptide mimetics that are structurally similar to therapeutically useful peptides may be used to produce an equivalent or enhanced therapeutic or prophylactic effect. Generally, peptidomimetics are structurally similar to a paradigm polypeptide (i.e., a polypeptide that has a biological or pharmacological activity), such as a naturally occurring αvβ5 ligand, but have one or more peptide linkages optionally replaced by a linkage selected from the group consisting of, e.g., —CH2NH—, —CH2S—, —CH2-CH2-, —CH=CH— (cis and trans), —COCH2-, —CH(OH)CH2-, and —CH2SO—. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity.

As used herein, the terms "nucleic acid" and "polynucleotide" are used interchangeably. Use of the term "polynucleotide" includes oligonucleotides (i.e., short polynucleotides). This term also refers to deoxyribonucleotides, ribonucleotides, and naturally occurring variants, and can also refer to synthetic and/or non-naturally occurring nucleic acids (i.e., comprising nucleic acid analogues or modified backbone residues or linkages), such as, for example and without limitation, phosphorothioates, phosphoramidates, methyl phosphonates, chiral-methyl phosphonates, 2-O-methyl ribonucleotides, peptide-nucleic acids (PNAs), and the like. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (see, e.g., Batzer et al., *Nucleic Acid Res.* 19:5081 (1991); Ohtsuka et al., *J. Biol. Chem.* 260:2605-2608 (1985); and Cassol et al. (1992); Rossolini et al., *Mol. Cell. Probes* 8:91-98 (1994)).

An "siRNA" or "RNAi" refers to a nucleic acid that forms a double stranded RNA, which double stranded RNA has the ability to reduce or inhibit expression of a gene or target gene when the siRNA expressed in the same cell as the gene or target gene (see, e.g., Bass, *Nature*, 411, 428-429 (2001); Elbashir et al., *Nature*, 411, 494-498 (2001); WO 00/44895; WO 01/36646; WO 99/32619; WO 00/01846; WO 01/29058; WO 99/07409; and WO 00/44914). "siRNA" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is 15-50 nucleotides in length, and the double stranded siRNA is about 15-50 base pairs in length, preferably about preferably about 20-30 base nucleotides, preferably about 20-25 nucleotides in length, e.g., 20, 21, 22, 23, 24, 25, 26, 27, 28, 29, or 30 nucleotides in length.

"Silencing" or "downregulation" refers to a detectable decrease of transcription and/or translation of a target sequence, i.e., the sequence targeted by the RNAi, or a decrease in the amount or activity of the target sequence or protein in comparison to the normal level that is detected in the absence of the interfering RNA or other nucleic acid sequence. A detectable decrease can be as small as 5% or 10%, or as great as 80%, 90% or 100%. More typically, a detectable decrease ranges from 20%, 30%, 40%, 50%, 60%, or 70%.

III. Inhibition of αvβ5 Activity

The present invention provides methods for treating or preventing diseases involving αvβ5 integrin such as, e.g., sepsis, by inhibiting binding of ligands to αvβ5 integrin. Any method that inhibits αvβ5 integrin expression or ligand binding to αvβ5 integrin can be used to treat diseases involving αvβ5 integrin according to the methods of the invention. For example, antibodies that specifically bind to αvβ5 integrin, antibodies that specifically bind to the β5 subunit, ligands of αvβ5 integrin, and peptide, non-peptide, and peptidomimetic analogs of such ligands can be used to inhibit binding to αvβ5 integrin and thus, treat or prevent diseases involving αvβ5. In addition, polynucleotides that inhibit expression of β5 (e.g., siRNA molecules, antisense sequences, etc.) can be used to treat or prevent diseases involving αvβ5 integrin, such as sepsis.

Integrin subunits are promiscuous, binding both to different dimer partners and different ligands. Different dimer pairs can bind to different, but often overlapping, sets of ligands and tissues. For example, the αv subunit can pair with several β integrin subunits, e.g., β1, β3, β5, β6, and β8. αvβ5 integrin binds with varying affinity to, e.g., $β_{Ig-h3}$, vitronectin, osteopontin, CXCL4, etc. αvβ1, αvβ3, and αvβ5 integrins can have overlapping tissue binding patterns, e.g., in arteriovenous malformations and cavernous malformations in the brain (Seker et al. (2006) *Neurosurgery* 58:159-68). Osteopontin is an example of a ligand that binds with varying affinity to α5β1, αvβ3, αvβ5, α9β1, and αvβ6. Sdc-1 (syndecan-1), vitronectin, and fibronectin also bind to multiple integrin pairs.

Thus, while there may be similar localization or apparent binding redundancy between particular integrin pairs, there are also clearly differences, as illustrated herein. Integrins are not functionally interchangeable, and therefore modulators of particular integrins are not expected to have interchangeable functions. In addition, given the promiscuity between ligands, and varying binding affinities, targeting a particular ligand does not predictably or entirely target its interactions with integrins.

In this regard, antibodies are particularly useful for targeting specific integrins because of their extraordinary specificity. Antibodies can be raised against a specific target, and recognize (specifically bind) a unique, three-dimensional epitope on the target.

A. αvβ5 Antibody Antagonists

Antibodies that specifically bind to αvβ5 integrin or to the β5 subunit of αvβ5 integrin can be used to treat or prevent sepsis. The antibody can also compete with other ligands for binding to αvβ5 integrin or to the β5 subunit of the αvβ5 integrin. Suitable antibodies include, but are not limited to monoclonal antibodies, humanized antibodies, chimeric antibodies, and antibody fragments (i.e., Fv, Fab, (Fab')$_2$, or scFv). In some embodiments, the antibodies of the invention do not bind other integrins, e.g., αvβ3, αvβ6, or αvβ8. In some embodiments, the antibodies of the invention include ALULA and antibodies that compete for αvβ5 binding with ALULA, and chimeric and fragment forms thereof.

As demonstrated herein, integrins αvβ3 and αvβ5 have opposing actions in the sepsis reaction. Antibodies specific for αvβ5 effectively prolong survival in two different murine sepsis models, while antibodies against αvβ3 actually reduce survival. Similarly, β5 deficient mice survived better with a less severe sepsis reaction (e.g., reduced vascular permeability and extravisation), while β3 deficient mice demonstrated a more severe sepsis reaction (e.g., increased vascular permeability and extravisation).

For treatment of sepsis, the invention provides antibodies that specifically bind to αvβ5, without significant binding of αvβ3. In some cases, the antibody does not bind to β3, β6, or β8 integrins. Binding is typically compared within a species, e.g., so that if the antibody is specific for human αvβ5, it does not significantly bind to human β3, β6, or β8 integrins. In some embodiments, the antibody has very low affinity for αvβ3, e.g. with $K_D$ of more than 0.1 mM. The antibody can specifically target β5, an epitope of αv that is present only when paired with β5, or an epitope that includes portions of βv and β5. In some embodiments, the αvβ5 specific antibody inhibits the interaction of αvβ5 with ligands that promote vascular permeability.

An antibody that specifically detects αvβ5 but not β3, β6, or β8 integrins can be detected using standard techniques described herein. Genbank accession numbers for exemplary amino acid sequences include the mouse and human β3 (O54890 and P05106.2), mouse and human β5 (P11688 and P18084), mouse and human β6 (Q9Z0T9 and P18564.2), and mouse and human β8 (P26012 and Q0VBD0). Integrin sequences for other species, e.g., non-human primates, rats, dogs, cats, horses, bovines, etc., are also publically available.

An antibody that specifically detects αvβ5, but not β3, β6, or β8, refers to binding of the integrin proteins from a particular species. For example, if an antibody according to the invention is specific for human αvβ5, but not β3, β6, or β8 integrin subunits, it does not significantly bind to human β3, β6, or β8.

In some embodiments, the monoclonal antibody ALULA (produced by the hybridoma deposited under ATCC Deposit No. PTA-5817, made Feb. 13, 2004, at the ATCC, 10801 University Blvd. Manassas, Va. 20110-2209), which binds to αvβ5 integrin, is used to treat or prevent diseases involving αvβ5 integrin, including sepsis. In some embodiments, humanized or chimeric ALULA, ALULA antibody fragments, or a monoclonal antibody which competes with ALULA for binding to αvβ5 integrin or the β5 subunit of the αvβ5 integrin is used to treat sepsis. Antibodies that compete for binding to αvβ5 integrin can be derived using the CDR sequences or V region sequences of ALULA. In some embodiments, competing antibodies are be identified by screening for antibodies that compete with ALULA.

ALULA binds to αvβ5 integrin and administration of ALULA to a mammalian subject reduces the severity of sepsis in the subject. In some embodiments, ALULA is a mouse IgG2b isotype monoclonal antibody specific for αvβ5. In some embodiments, an αvβ5 binding fragment of ALULA is used, e.g., the Fab' region, or a humanized Fab' region that retains the CDRs of ALULA, or similar sequences that bind to αvβ5. ALULA does not significantly bind to epitopes that include β3, β6, or β8 integrins (Su et al. (2007) *Am J Respir Cell Mol Biol* 36:377). ALULA can be chimeric or humanized using techniques common in the art.

Monoclonal antibodies are obtained by various techniques familiar to those skilled in the art. Briefly, spleen cells from an animal immunized with a desired antigen are immortalized, commonly by fusion with a myeloma cell (see, for example, Kohler & Milstein, *Eur. J. Immunol.* 6: 511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science* 246: 1275-1281 (1989).

Monoclonal antibodies are collected and titered against the immunogen in an immunoassay, for example, a solid phase immunoassay with the immunogen immobilized on a solid support. Monoclonal antibodies will usually bind with a $K_d$ of at least about 0.1 mM, more usually at least about 1 µM, and can often be designed to bind with a $K_d$ of 1 nM or less.

In an exemplary embodiment, an animal, such as a rabbit or mouse is immunized with αvβ5 polypeptide, or an nucleic acid construct encoding such a polypeptide. The antibodies produced as a result of the immunization can be isolated using standard methods.

The immunoglobulins, including binding fragments and other derivatives thereof, of the present invention may be produced readily by a variety of recombinant DNA techniques, including by expression in transfected cells (e.g., immortalized eukaryotic cells, such as myeloma or hybridoma cells) or in mice, rats, rabbits, or other vertebrate capable of producing antibodies by well known methods. Suitable source cells for the DNA sequences and host cells for immunoglobulin expression and secretion can be obtained from a number of sources, such as the American Type Culture Collection (Catalogue of Cell Lines and Hybridomas, Fifth edition (1985) Rockville, Md.).

In some embodiments, the antibody is a humanized antibody, i.e., an antibody that retains the reactivity of a non-human antibody while being less immunogenic in humans. This can be achieved, for instance, by retaining the non-human CDR regions that are specific for αvβ5 integrin, and replacing the remaining parts of the antibody with their human counterparts. See, e.g., Morrison et al., *PNAS USA*, 81:6851-6855 (1984); Morrison and Oi, *Adv. Immunol.*, 44:65-92 (1988); Verhoeyen et al., *Science*, 239:1534-1536 (1988); Padlan, *Molec. Immun.*, 28:489-498 (1991); Padlan, *Molec. Immun.*, 31(3):169-217 (1994). Techniques for humanizing antibodies are well known in the art and are described in e.g., U.S. Pat. Nos. 4,816,567; 5,530,101; 5,859,205; 5,585,089; 5,693,761; 5,693,762; 5,777,085; 6,180,370; 6,210,671; and 6,329,511; WO 87/02671; EP Patent Application 0173494; Jones et al. (1986) *Nature* 321:522; and Verhoyen et al. (1988) *Science* 239:1534. Humanized antibodies are further described in, e.g., Winter and Milstein (1991) *Nature* 349:293. For example, polynucleotides comprising a first sequence coding for humanized immunoglobulin framework regions and a second sequence set coding for the desired immunoglobulin complementarity determining regions can be produced synthetically or by combining appropriate cDNA and genomic DNA segments. Human constant region DNA sequences can be isolated in accordance with well known procedures from a variety of human cells. The CDRs for producing the immunoglobulins of the present invention will be similarly derived from monoclonal antibodies capable of specifically binding to αvβ5 integrin (e.g., ALULA or antibodies that compete with ALULA for specific binding to αvβ5 integrin).

In some cases, transfer of a CDR to a human framework leads to a loss of specificity for the humanized antibody. In these cases, back mutation can be introduced into the framework regions of the human portion of the antibody. Methods of making back mutations are well known in the art and are described in, e.g., Co et al., *PNAS USA* 88; 2269-2273 (1991) and WO 90/07861.

The αvβ5 specific antibody can also be chimeric, so that all or most of the variable region is retained, but the constant region replaced. Using ALULA as an example, the murine variable region, that possesses αvβ5 integrin binding activity, is combined with human constant regions, or constant regions from another mammal for use in veterinary treatments.

In some embodiments, the antibodies are antibody fragments such as Fab, F(ab')$_2$, Fv or scFv. The antibody fragments can be generated using any means known in the art including, chemical digestion (e.g., papain or pepsin) and recombinant methods. Methods for isolating and preparing recombinant nucleic acids are known to those skilled in the art (see, Sambrook et al., *Molecular Cloning. A Laboratory Manual* (2d ed. 1989); Ausubel et al., *Current Protocols in Molecular Biology* (1995)). The antibodies can be expressed in a variety of host cells, including *E. coli*, other bacterial hosts, yeast, and various higher eukaryotic cells such as the COS, CHO, and HeLa cells lines and myeloma cell lines.

One embodiment of the invention provides methods for identifying antibodies that compete with ALULA for specific binding to αvβ5 integrin.

Competitive binding assays can be used to identify antibodies that compete with ALULA for specific binding to αvβ5 integrin. Any of a number of competitive binding assays known in the art can be used to measure competition between two antibodies to the same antigen. Briefly, the ability of different antibodies to inhibit the binding of another antibody is tested. For example, antibodies can be differentiated by the epitope to which they bind using a sandwich ELISA assay. This is carried out by using a capture antibody to coat the surface of a well. A subsaturating concentration of tagged-antigen is then added to the capture surface. This protein will be bound to the antibody through a specific antibody:epitope interaction. After washing a second antibody, which has been covalently linked to a detectable moiety (e.g., HRP, with the labeled antibody being defined as the detection antibody) is added to the ELISA. If this antibody recognizes the same epitope as the capture antibody it will be unable to bind to the target protein as that particular epitope will no longer be available for binding. If however this second antibody recognizes a different epitope on the target protein it will be able to bind and this binding can be detected by quantifying the level of activity (and hence antibody bound) using a relevant substrate. The background is defined by using a single antibody as both capture and detection antibody, whereas the maximal signal can be established by capturing with an antigen specific antibody and detecting with an antibody to the tag on the antigen. By using the background and maximal signals as references, antibodies can be assessed in a pair-wise manner to determine epitope specificity.

A first antibody is considered to competitively inhibit binding of a second antibody, if binding of the second antibody to the antigen is reduced by at least 30%, usually at least about 40%, 50%, 60% or 75%, and often by at least about 90%, in the presence of the first antibody using any of the assays described above.

B. Inhibiting Expression of αvβ5 Integrin

As discussed above, the present invention is based on the surprising discovery that blocking binding of ligands to αvβ5 integrin reduces the severity of sepsis. For example, as described in the examples below, the inventors have demonstrated that β5$^{-/-}$ mice, and mice treated with an αvβ5 antagonist antibody, have improved survival in a sepsis model. Antibody antagonists to αvβ3 were actually harmful, and aggravated the septic response.

Therefore, a nucleotide sequence that specifically interferes with expression of the β5 integrin gene at the transcriptional or translational level can be used to treat or prevent sepsis. This approach may utilize, for example, siRNA and/or antisense oligonucleotides to block transcription or translation of a specific mutated mRNA, either by inducing degradation of the mRNA with a siRNA or by masking the mRNA with an antisense nucleic acid. In some embodiments, the siRNA or antisense construct does not significantly block expression of the β3 subunit.

1. siRNA

Double stranded siRNA that corresponds to the β5 gene, can be used to silence the transcription and/or translation of αvβ5 integrin by inducing degradation of β5 mRNA transcripts, and thus treat or prevent sepsis by preventing expression of αvβ5 integrin. The siRNA is typically about 5 to about 100 nucleotides in length, more typically about 10 to about 50 nucleotides in length, most typically about 15 to about 30 nucleotides in length. siRNA molecules and methods of generating them are described in, e.g., Bass, 2001, *Nature*, 411, 428-429; Elbashir et al., 2001, *Nature*, 411, 494-498; WO 00/44895; WO 01/36646; WO 99/32619; WO 00/01846; WO 01/29058; WO 99/07409; and WO 00/44914. A DNA molecule that transcribes dsRNA or siRNA (for instance, as a hairpin duplex) also provides RNAi. DNA molecules for transcribing dsRNA are disclosed in U.S. Pat. No. 6,573,099, and in U.S. Patent Application Publication Nos. 2002/0160393 and 2003/0027783, and Tuschl and Borkhardt, *Molecular Interventions*, 2:158 (2002). For example, dsRNA oligonucleotides that specifically hybridize to the nucleic acid sequences set forth in Genbank Accession Nos.: AK054968; BF588784; BE208820; BE207859; or BE206567 can be used in the methods of the present invention. A decrease in the severity of sepsis symptoms in comparison to symptoms detected in the absence of the interfering RNA can be used to monitor the efficacy of the siRNA.

siRNA can be delivered to the subject using any means known in the art, including by injection, inhalation, or oral ingestion of the siRNA. Another suitable delivery system for siRNA is a colloidal dispersion system such as, for example, macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. Nucleic acids, including RNA and DNA within liposomes and be delivered to cells in a biologically active form (Fraley, et al., *Trends*

*Biochem. Sci.*, 6:77, 1981). Liposomes can be targeted to specific cell types or tissues using any means known in the art.

2. Antisense Oligonucleotides

Antisense oligonucleotides that specifically hybridize to nucleic acid sequences encoding β5 polypeptides can also be used to silence the transcription and/or translation of αvβ5 integrin, and thus treat or prevent sepsis. For example, antisense oligonucleotides that specifically hybridize to the nucleic acid sequences set forth in Genbank Accession Nos.: BF588784 (human); BE208820 (human); BE207859 (human); BE206567 (human); NM_002213 (human); BC006541 (human); NM_174679 (bovine); AF468059 (bovine); NM_010580 (murine); BC058246 (murine); XM_147237 (murine); AF022111 (murine); AF022110 (murine); AF043257 (murine); AF043256 (murine); and 558644 (rat) can be used in the methods of the present invention. A decrease in the severity of sepsis symptoms in comparison to symptoms detected in the absence of the antisense nucleic acids can be used to monitor the efficacy of the antisense nucleic acids.

Antisense nucleic acids are DNA or RNA molecules that are complementary to at least a portion of a specific mRNA molecule (see, e.g., Weintraub, Scientific American, 262:40 (1990)). Typically, synthetic antisense oligonucleotides are generally between 15 and 25 bases in length. Antisense nucleic acids may comprise naturally occurring nucleotides or modified nucleotides such as, e.g., phosphorothioate, methylphosphonate, and -anomeric sugar-phosphate, backbone-modified nucleotides.

In the cell, the antisense nucleic acids hybridize to the corresponding mRNA, forming a double-stranded molecule. The antisense nucleic acids, interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target nucleotide mutant producing cell. The use of antisense methods to inhibit the in vitro translation of genes is well known in the art (Marcus-Sakura, *Anal. Biochem.*, 172:289, (1988)). Less commonly, antisense molecules which bind directly to the DNA may be used.

Delivery of antisense polynucleotides specific for the 135 integrin gene can be achieved using any means known in the art including, e.g., direct injection, inhalation, or ingestion of the polynucleotides. In addition, antisense polynucleotides can be delivered using a recombinant expression vector (e.g., a viral vector based on an adenovirus, a herpes virus, a vaccinia virus, or a retrovirus) or a colloidal dispersion system (e.g., liposomes) as described herein.

IV. Identifying Additional αvβ5 Antagonists

Additional antagonists of αvβ5 integrin can be found in US Application No. 20050226865 or can be readily identified according to methods well known to those of skill in the art. One convenient method for screening for antagonists involves measuring the ability of the potential antagonists to compete for binding of a known ligand of the integrin. For example, vitronectin, fibronectin, osteopontin, tenascin c and adenovirus penton base are known ligands of αvβ5 integrin that can be used in competition assays to identify potential antagonists of αvβ5 integrin. Other polypeptides comprising the amino acid sequence RGD can also be used in competition assays. In addition, monoclonal antibodies and fragments thereof that bind to αvβ5 integrin can be used to screen for additional antagonists of αvβ5 integrin. In some embodiments, ALULA and antibodies that compete with ALULA for binding to αvβ5 are used to screen for additional antagonists of αvβ5 integrin.

Competition assays are well known in the art. Typically, a ligand of αvβ5 integrin or an antibody that competes for ligand binding to αvβ5 integrin (e.g., ALULA) is labeled so that differences in binding to αvβ5 integrin (e.g., in the presence of increasing amount of a potential competing ligand for αvβ5 integrin) can be measured. The ligands may be naturally occurring ligands as well as synthetic ligands. Competition assays indicate the affinity of potential competitor antagonists.

A number of different screening protocols can be utilized to identify agents that modulate the level of activity or function of a particular topology of αvβ5 integrin in cells, e.g., in mammalian cells, and especially in human cells. In general teems, the screening methods involve screening a plurality of agents to identify an agent that interacts with αvβ5, for example, by binding to αvβ5 integrin or preventing an antibody (e.g., ALULA) or ligand specific for αvβ5 integrin (e.g., vitronectin, fibronectin, osteopontin, tenascin c, adenovirus penton base) from binding to αvβ5 integrin.

Preliminary screens can be conducted by screening for agents capable of binding to αvβ5 integrin, as at least some of the agents so identified are likely αvβ5 integrin antagonists. The binding assays usually involve contacting αvβ5 integrin with one or more test agents and allowing sufficient time for αvβ5 integrin and test agents to form a binding complex. Any binding complexes formed can be detected using any of a number of established analytical techniques. Protein binding assays include, but are not limited to, immunohistochemical binding assays, flow cytometry or other assays. The αvβ5 integrin utilized in such assays can be naturally expressed, cloned or synthesized.

The screening methods of the invention can be performed as in vitro or cell-based assays. Cell based assays can be performed in any cells in which αvβ5 integrin is expressed. Cell-based assays may involve whole cells or cell fractions containing αvβ5 integrin to screen for agent binding or modulation of αvβ5 integrin activity by the agent. One of skill in the art will appreciate that αvβ5 integrin can be expressed in cells that do not contain endogenous αvβ5 integrin. Suitable cell-based assays are described in, e.g., DePaola et al., *Annals of Biomedical Engineering* 29: 1-9 (2001).

Agents that are initially identified as interacting with αvβ5 integrin can be further tested to validate the apparent activity. Preferably such studies are conducted with suitable cell-based or animal models of sepsis as described in the examples below. The basic format of such methods involves administering a lead compound identified during an initial screen to an animal that serves as a model and then determining if in fact the sepsis is ameliorated. The animal models utilized in validation studies generally are mammals of any kind. Specific examples of suitable animals include, but are not limited to, primates (e.g., chimpanzees, monkeys, and the like) and rodents (e.g., mice, rats, guinea pigs, rabbits, and the like).

The agents tested as potential antagonists of αvβ5 integrin can be any small chemical compound, or a biological entity, such as a polypeptide, sugar, nucleic acid or lipid. Alternatively, modulators can be genetically altered versions of αvβ5 integrin or an αvβ5 integrin ligand. Essentially any chemical compound can be used as a potential modulator or ligand in the assays of the invention, although most often compounds that can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays).

In one embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science*, 274: 1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., ECIS™, Applied Bio-Physics Inc., Troy, N.Y., MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

V. Therapeutic Treatment

As discussed above, the invention also provides compositions comprising antagonists of $\alpha v \beta 5$ integrin. The compositions of the invention can be provided to treat or prevent diseases which involve $\alpha v \beta 5$ integrins including sepsis.

In one embodiment, the compositions of the invention (e.g., compositions comprising ALULA, humanized ALULA, ALULA fragments, or antibodies that compete for $\alpha v \beta 5$ binding with ALULA) can be provided to treat or prevent sepsis in subjects with sepsis or at risk for developing sepsis. For example, a subject having had exposure to an infective agent would likely be treated after such exposure, whereas a patient at risk of sepsis can be treated prophylactically and/or therapeutically. Examples of patients at risk of sepsis include patients with acute aspiration, patients exhibiting symptoms of bacterial sepsis, patients whose blood cultures are positive for gram positive or gram negative bacteria, patients with pancreatitis, or patients in hemorrhagic shock.

The compositions of the invention can be administered in a single dose, multiple doses, or on a regular basis (e.g., daily) for a period of time (e.g., 2, 3, 4, 5, 6, days or 1-3 weeks or more).

The compositions of the invention can be administered directly to the mammalian subject to block $\alpha v \beta 5$ binding using any route known in the art, including e.g., by injection (e.g., intravenous, intraperitoneal, subcutaneous, intramuscular, or intradermal), inhalation, transdermal application, rectal administration, or oral administration.

The pharmaceutical compositions of the invention may comprise a pharmaceutically acceptable carrier. Pharmaceutically acceptable carriers are determined in part by the particular composition being administered, as well as by the particular method used to administer the composition. Accordingly, there are a wide variety of suitable formulations of pharmaceutical compositions of the present invention (see, e.g., Remington's Pharmaceutical Sciences, 17th ed., 1989).

The compositions of the invention, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, orally, nasally, topically, intravenously, intraperitoneally, or intrathecally. The formulations of compounds can be presented in unit-dose or multi-dose sealed containers, such as ampoules and vials. Solutions and suspensions can be prepared from sterile powders, granules, and tablets of the kind previously described. The modulators can also be administered as part a of prepared food or drug.

Formulations suitable for oral administration can comprise: (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The dose administered to a patient, in the context of the present invention should be sufficient to effect a beneficial response in the subject over time, e.g., a reduction in pulmonary capillary hydrostatic pressure, a reduction in fluid in the lungs, a reduction in the rate of fluid accumulation in the lungs, or a combination thereof. The optimal dose level for any patient will depend on a variety of factors including the efficacy of the specific modulator employed, the age, body weight, physical activity, and diet of the patient, on a possible combination with other drugs, and on the severity of the sepsis. The size of the dose also will be determined by the existence, nature, and extent of any adverse side-effects that accompany the administration of a particular compound or vector in a particular subject.

In determining the effective amount of the antagonists of αvβ5 integrin to be administered a physician may evaluate circulating plasma levels of the antagonist and antagonist toxicity. In general, the dose equivalent of an antagonist is from about 1 ng/kg to 10 mg/kg for a typical subject.

For administration, the antagonists of αvβ5 integrin can be administered at a rate determined by the $LD_{50}$ of the antagonist, and the side-effects of the antagonist at various concentrations, as applied to the mass and overall health of the subject. Administration can be accomplished via single or divided doses.

VI. Combination Therapy

In some embodiments, an antagonist of αvβ5 integrin is administered in conjunction with a second therapeutic agent for treating or preventing sepsis. For example, an antagonist of αvβ5 integrin (e.g., ALULA, humanized ALULA, fragments of ALULA, or an antibody that competes for αvβ5 with ALULA) can be administered in conjunction with any of the standard treatments for sepsis including, e.g., antibiotics, statins, steroids, activated Protein C, diuretic agents, vasoconstrictors, or inotropic drugs. In addition, an antagonist of αvβ5 integrin may be administered in conjunction with agents that target metabolic pathways that are implicated in sepsis. For example, an antagonist of αvβ5 integrin may be administered in conjunction with TGFβ pathway inhibitors, activated Protein C, GM-CSF, antibodies that specifically bind to αvβ5 integrin or β5, a second antagonist of αvβ5 integrin, antibodies that specifically bind to a αvβ6 integrin, antagonists of αvβ6 integrin, thrombin receptor antagonists, anti-thrombin agents, rho kinase inhibitors, and nucleic acids that inhibit expression of αvβ5 integrin including e.g., the antisense oligonucleotides and siRNA described herein.

Statins (HMG-CoA reductase inhibitors) include, e.g., simvastatin or atorvastatin. Antibiotic therapies are common, and can best be selected by the medical professional to specifically target a particular infection. Exemplary antibiotics include, e.g., penicillin, erythromycin, cyclic lipopeptides (daptomycin), glycylcyclines (tigecycline), and oxazolidinones (linezolid).

Suitable TGFβ pathway inhibitors include, e.g., TGF-β antibodies (including those that specifically block TGF-β1, TGF-β2, TGF-β3 or any combination thereof) as described in e.g., Ling et al., *J. Amer. Soc. Nephrol.* 14: 377-388 (2003), McCormick et al., *J. Immunol.* 163:5693-5699 (1999), and Cordeiro, *Curr. Opin. Mol. Ther.* 5(2):199-203 (2003); TGF-β receptor type II inhibitors or TGF-β receptor type I kinase inhibitors as described in, e.g., DaCosta Bayfield, *Mol. Pharmacol.* 65(3):744-52 (2004), Laping, *Curr. Opin. Pharmacol.* 3(2):204-8 (2003), Laping, *Mol. Pharmacol.* 62(1):58-64 (2002); soluble TGF-β receptor type II as described in, e.g., Pittet, *J. Clin. Invest.* 107:1537-1544 (2001); Wang et al., *Exp Lung Res.* 28(6):405-17 (2002) and Wang, *Thorax* 54(9):805-12 (1999); soluble latency associated peptides as described in, e.g., Zhang, *J. Invest. Dermatol.* 121(4):713-9 (2003); thrombospondin I inhibitors as described in, e.g., Crawford et al., *Cell* 93:1159-1170 (1998), Riberiro et al., *J. Biol. Chem.* 274: 13586-13593 (1999), and Schultz-Cherry et al., *J. Biol. Chem.* 269: 26775-26782 (1994). Suitable β-2 agonists include, e.g., albuterol, bitolterol, formoterol, isoproterenol, levalbuterol, metaproterenol, pirbuterol, salmeterol, and terbutaline.

In addition, the antagonist of αvβ5 integrin can be administered in combination with a β2 adrenergic receptor as described in U.S. Patent Publication No. 20020004042, and with small molecule inhibitors for αvβ5 integrins as described in, e.g., US Published Patent Application Nos. 2000/40019206, 2004/0019037, 2004/0019035, 2004/0018192, 2004/0010023, 2003/0181440, 2003/0171271, 2003/0139398, 2002/0037889, 2002/0077321, and 2002/0072500.

The antagonist of αvβ5 integrin (e.g., ALULA, humanized or chimeric ALULA, fragments of ALULA, or an antibody that competes for αvβ5 binding with ALULA) and the second therapeutic agent may be administered simultaneously or sequentially. For example, the antagonist of αvβ5 integrin may be administered first, followed by the second therapeutic agent. Alternatively, the second therapeutic agent may be administered first, followed by the antagonist of αvβ5 integrin. In some cases, the antagonist of αvβ5 integrin and the second therapeutic agent are administered in the same formulation. In other cases the antagonist of αvβ5 integrin and the second therapeutic agent are administered in different formulations. When the antagonist of αvβ5 integrin and the second therapeutic agent are administered in different formulations, their administration may be simultaneous or sequential.

For administration, the antagonists of αvβ5 integrin and second therapeutic agent can be administered at a rate determined by the combined $LD_{50}$ of the antagonist and the second therapeutic agent, and the side-effects of the antagonist and the second therapeutic agent at various concentrations, as applied to the mass and overall health of the subject. In some cases, the antagonists of αvβ5 integrin and second therapeutic agent are each administered at a subtherapeutic dose or a therapeutic dose.

EXAMPLES

Example 1: Materials and Methods

Reagents and Antibodies:

LPS (List Pharmaceuticals), VEGF and TGF-β (R & D Systems), thrombin (Amersham Biosciences). Mouse anti-human αvβ3 antibody (clone LM609) (Chemicon) and mouse IgG1 isotype control (Upstate). Mouse anti-mouse/human αvβ5 antibody (ALULA), courtesy of Amha Atakilit (Su et al. 2007 *Am J Respir Cell Mol Biol* 36:377) and C7 (anti-bovine LDL receptor IgG2b isotype control (ATCC). $^{125}$I-labeled bovine serum albumin (BSA) (Jeanatope ISO-TEX Diagnostics), $^{14}$C-BSA) (Perkin-Elmer). Sphingosine 1-phosphate (S1P) (Sigma).

Cell Culture:

Human pulmonary artery endothelial cells (HPAECs) and human umbilical vein endothelial cells (HUVECs) were cultured and maintained according to manufacturer protocols in EGM-2™ media (Clonetics, Lonza).

Assay of Transendothelial Albumin Flux:

Cells were seeded onto 6.5-mm collagen-coated PFTE membrane Costar Transwells (Fisher Scientific) at 75,000 cells per well and cultured to confluence. Cells were incubated with antibodies and reagents as described in the text. Afterwards, $^{14}$C-BSA (0.005 µCi) (Perkin-Elmer) was applied to each upper compartment for 1 h at 37° C., after which contents from the lower compartment were collected and counted with an LS 6500 Multi-Purpose Scintillation Counter (Beckman). Only monolayers retaining >97% of tracer at baseline were studied.

Actin Cytoskeleton Staining:

Cells were grown on collagen-coated glass coverslips to confluence over 4 days. The cells were serum-starved cells (12 h) and pre-treated with antibodies and reagents as described in the text. The cells were then fixed with 3.7% paraformaldehyde for 10 min, permeabilized with 0.5% triton X-100, then stained with rhodamine phalloidin (Molecular Probes), mounted, and imaged using a Leica DM5000B microscope equipped for epifluorescence.

β3 Subunit k.o., β5 Subunit k.o., and WT Mice:

129/sv background β3 and β5 subunit k.o. and WT mice were bred and maintained in our laboratory. All experiments were performed with age and weight-matched female mice weighing 20 g (+/−2 g).

Intraperitoneal (i.p.) LPS Sepsis Model:

LPS (List Pharmaceuticals) diluted 1 mg/ml in water is injected i.p. at a dose of 10 mg/kg or 13 mg/kg.

Organ Extravascular Permeability Assay:

At a predetermined time point after application of the respective septic insult (approximately 36 hours for i.p. LPS) 0.5 µCi of $^{125}$I-BSA were injected retroorbitally and allowed to circulate for 2 hours. After two hours the mice were euthanized and organs harvested for individual assessment of $^{125}$I counts per minute (CPM) (Wizard® γ counter, PerkinElmer). Organs harvested included the small intestine/mesentery, colon. Lung vascular permeability will be assessed simultaneously, using methods to measure extravascular plasma equivalents (EVPE) as described in our previous methods (Su et al. 2007 µm *J Respir Cell Mol Biol* 36:377).

FITC-BSA Localization of Mesenteric Plasma Leakage:

Sites of endothelial leakage were identified microscopically by injecting FITC-labeled BSA (90S Sigma FD70S, 25 mg/ml stock) retroorbitally (100 mg/kg) 2 hours before the mouse was euthanized. Mesentery and small bowel was harvested en bloc taking care not to disrupt vasculature. Mesenteric whole mounts were prepared and fixed with 4% paraformaldehyde and PBS 0.3% Triton (Baluk et al. (1999) *Br J Pharmacol* 126:522). Sites of leakage were identified as areas of local FITC extravasation using a Leica DM5000B microscope.

Bone Marrow Reconstitution:

6-8 week old donor mice (either β3 k.o. or wildtype lines) were euthanized with isoflurane overdose and cervical dislocation. Bone marrow cells were harvested from distal ends of extremity long bones and suspended in IMDM 20% fetal calf serum media. 1-3×10$^6$ cells/recipient were injected by tail vein into irradiated (1,100 RADs, approximately 8 minutes) mice.

Irradiated mice were treated with neomycin/polymycin water for 6 weeks post-procedure. Bone marrow engraftment was determined by flow cytometry for β3 expression on platelets.

Mouse Platelet Isolation and Assessment of β3 Expression:

Blood was collected from mice by inferior vena caval puncture and added to tubes containing Walsh buffer (NaCl-137 nM, KCl 2.7 nM, MgCl2.6H2O 1.0 mM, NaH2PO$_4$.H2O 3.3 mM, HEPES 3.8 mM, glucose 0.1%, BSA 0.1%, pH 7.4) with ACD (Sigma). 10 units of apyrase plus 0.75 ul of PGE1 was added and suspension prior to centrifugation (200 g for 5 minutes). Plasma rich plasma was removed and 2.0 µl apyrase and 0.75 ul PGE1 added prior to centrifugation (700 g for 5 minutes). Pelleted platelets were then incubated with 133 antibodies (eBioscience anti-mouse CD61 Clone 2C9.G3, 16-0611-81) and labeled with anti-hamster PE secondary antibodies (Jackson Labs) and processed by flow cytometry (FACSort, Beckton Dickinson).

Hematocrit Measurements:

Blood was obtained via inferior venal caval puncture and aspirated into microhematocrit capillary tube and spun in a microcentrifuge (Unico C MH30).

Example 2: Agonist-Induced Permeability in Human Pulmonary Artery Endothelial Cells (HPAECs) is Attenuated by Antibody Inhibition of αvβ5 and Enhanced by Antibody Inhibition of αvβ3

HPAECs were treated with function-blocking antibodies specific for integrins αvβ5 and αvβ3 and the effects on edemagenic agonist-induced permeability were observed. Endothelial permeability was determined by measuring C$^{14}$-BSA flux across confluent monolayers grown on Transwells. αvβ5-inhibiting antibodies attenuated the increased permeability response to VEGF, TGF-β, and thrombin. In contrast, Avβ3-inhibiting antibodies enhanced the permeability response to each of these agonists (FIG. 1A).

Example 3: αvβ3 and αvβ5 Co-Localize at Focal Adhesions

Considering the opposing effects of αvβ5 and αvβ3 blockade on agonist-induced permeability, we immunocytochemically localized αvβ5 and αvβ3 in HPAECs to assess whether these functional differences could be associated with differential cellular distribution. Surprisingly, both integrins largely co-localized to common focal adhesion sites (FIG. 1B).

Example 4: αvβ5 Preferentially Supports Thrombin-Induced Stress Fiber Formation and Δvβ3 Preferentially Supports S1P-Induced Cortical Actin Formation Despite occupying common focal adhesions, we tested whether αvβ5 and αvβ3 could support differential patterns of actin organization in a manner consistent with observed functional effects. Thrombin is a procoagulant serine protease that has been studied extensively for its endothelial permeability-inducing properties. Thrombin signals through the $PAR_1$ G protein coupled receptor (GPCR) to initiate complex signaling pathways that activates RhoA and organizes F-actin into stress fibers. Sphingosine-1-phosphate (S1P) is a lipid produced by the breakdown of the membrane phospholipid sphingomyelin. Activation of the $S1P_1$ receptor, in contrast to $PAR_1$, triggers an endothelial barrier-protective response. $S1P_1$ activation leads to the p110α phosphoinositide 3-kinase (PI3K)-dependent recruitment of Tiam-1 into caveolin-enriched microdomains and activation of Rac1, which induces reorganization of actin into cortically distributed bundles, i.e. "cortical" actin.

We investigated the effects of antibody blockade of αvβ5 and αvβ3 on the functionally and morphologically distinct effects of thrombin and S1P on HPAECs. αvβ5 blockade attenuated stress fiber formation in HPAECs treated with thrombin. Integrin αvβ3 blocking antibodies had no effect (FIG. 1C). In contrast, S1P-induced cortical actin formation was not affected by αvβ5 antibodies, but rather, was attenuated by αvβ3 antibodies (FIG. 1D).

Example 5: αvβ3 Blockade Overcomes S1P Protection Against Thrombin-Induced Permeability We next studied the effects of αvβ3 blockade on the barrier-protective response induced by S1P. HPAECs pretreated with αvβ3 or isotype control antibodies, and then treated with S1P, were stimulated with increasing doses of thrombin. Pretreatment with αvβ3 antibodies overcame the barrier-protective response to S1P, and caused a hyperpermeable response to thrombin compared to cells pretreated with isotype control (FIG. 1E).

Example 6: β3 k.o. Mice have Increased Pulmonary Edema Formation in LPS-Induced Models of Acute Lung Injury (ALI)

Figure 2:
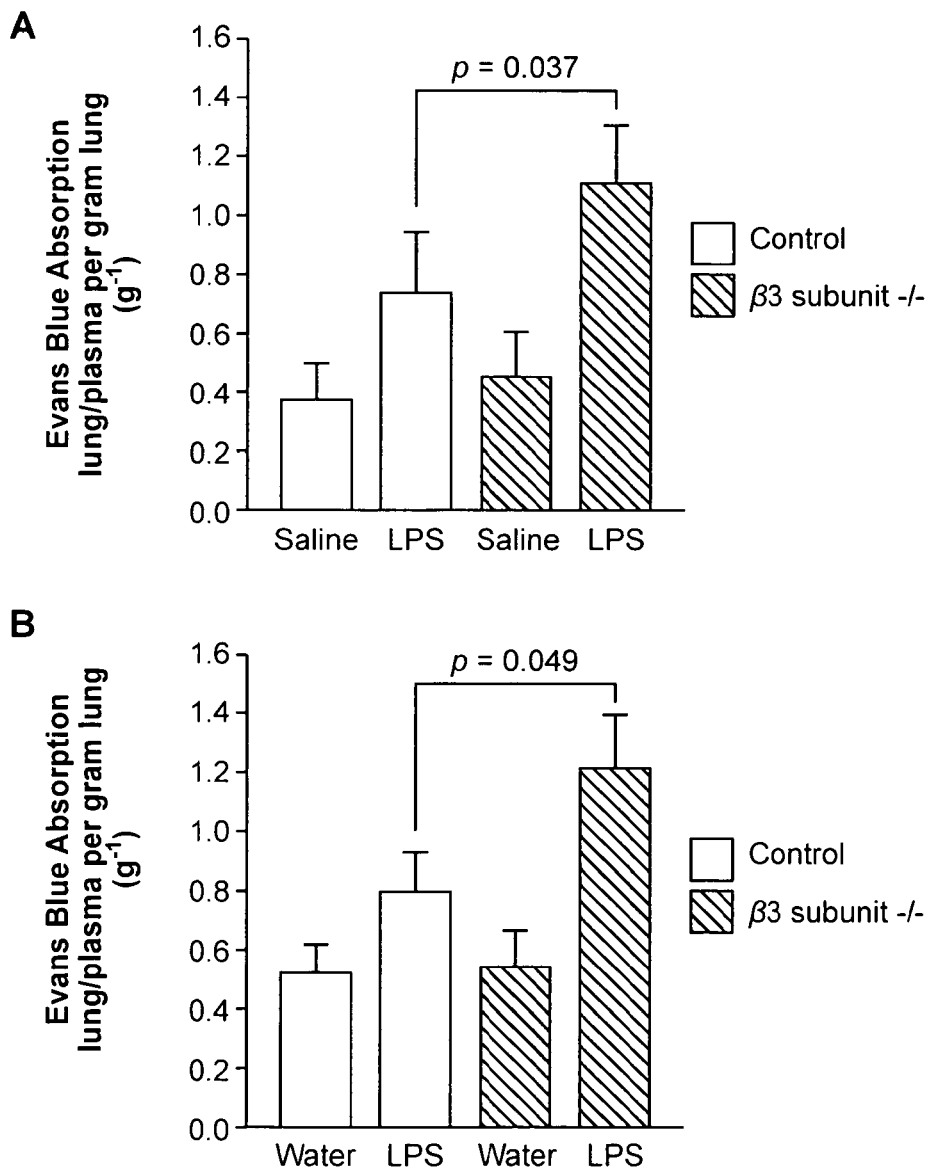
FIG. 2: β3 k.o. mice have increased pulmonary edema formation in LPS-induced models of ALI. Weight- and sex-matched β3 k.o. and wildtype mice were administered 50 µg LPS in 50 µl water vs. 50 µl water vehicle control, or 10 mg/kg vs. equal water volume control endotracheally (A), or 10 mg/kg i.p. (B). Five days after LPS or water administration, Evans blue dye was administered retroorbitally 2 hours prior to lung perfusion and en bloc lung harvest. Extravascular Evans blue was extracted with formamide and measured by spectrophotometry (560 nm). Evans blue extravasation measured as spectrophotometry units per dry weight of total lung ($g^{-1}$). Data shown are the means+/−standard errors, n=10.

Function-blocking αvβ5 antibodies attenuated lung edema formation in an ischemia-perfusion model of acute lung injury (ALI), and αvβ5 antibody-treated and 135 subunit k.o. mice are protected from lung edema formation in a ventilator-induced model of ALI (Su et al. (2007) *Am J Respir Cell Mol Biol* 36:377). To determine if the hyperpermeable endothelial response seen with αvβ3 blockade is relevant in models of ALI, we measured lung vascular permeability after endotracheal (FIG. 2A) and intraperitoneal (i.p.) (FIG. 2B) LPS administration in β3 k.o. mice vs. wildtype controls. In each of these models, we found a significant increase in lung Evans blue extravasation in the β3 k.o. group.

To determine if the protective effect of β5 deficiency applies to LPS-induced models of ALI, we measured Evans blue extravasation in lungs after endotracheal and i.p. LPS administration in β5 k.o. vs. wildtype mice. Preliminary results indicate that β5 k.o. mice have decreased pulmonary edema formation in LPS-induced models of ALI. Weight- and sex-matched β5 k.o. and wildtype mice were administered 50 μg LPS in 50 μl water vs. 50 μl water vehicle control, or 10 mg/kg i.p.

Figure 3:
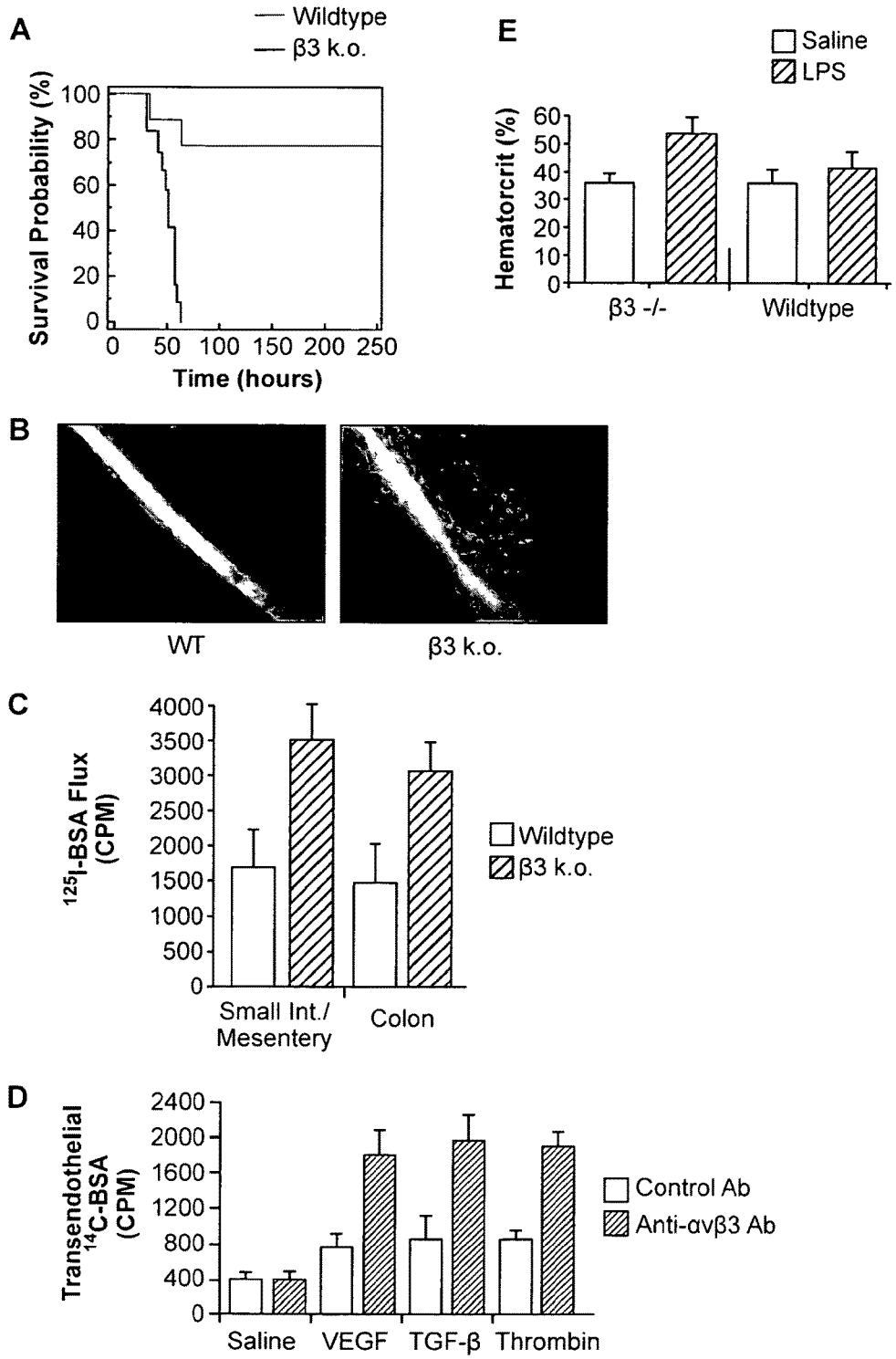
FIG. 3A: β3 k.o. mice have increased mortality in i.p. LPS-induced sepsis model compared to wildtype controls. Weight and sex-matched β3 k.o. and wildtype control mice were administered 10 mg/kg of LPS by i.p. injection. Data analyzed by Kaplan-Meier survival analysis, logrank test difference between groups, p=0.0044.
FIG. 3B: β3 k.o. mice have local extravasation of a FITC-BSA tracer around mesenteric vessels after i.p. injection of LPS (10 mg/kg). Sites of endothelial leakage were identified microscopically by using the FITC-labeled BSA (90 micron size, Sigma), which was injected retroorbitally (30 mg/kg in saline) one hour before the mouse was euthanized. Mesentery and small bowel was harvested en bloc taking care not to disrupt vasculature. Mesenteric whole mounts were prepared and fixed (Baluk et al. (1999) *Br J Pharmacol* 126:522). Sites of leakage were identified as areas of local FITC extravasation using a Leica DM5000B microscope.
FIG. 3C: β3 k.o. mice have increased extravasation of an $^{125}$I-BSA tracer in small bowel and mesentery and colon after i.p. injection of LPS (10 mg/kg). Weight and sex-matched β3 k.o. and wildtype control mice were administered 10 mg/kg of LPS by i.p. injection. At 30 hours, 0.5 µCi $^{125}$I-BSA was administered by retroorbital injection. After 2 hours, the mice were euthanized and small intestine and mesentery, and colon were harvested and analyzed for total counts per minute (CPM). Data shown are the means+/−standard errors, n=6 for each group. β3 k.o. vs. wildtype control: p=0.034 for small intestine/mesentery, p=0.042 for colon.
FIG. 3D: Agonist-induced permeability in human umbilical vein endothelial cells (HUVECs) is enhanced by antibody inhibition of Δvβ3. Serum-starved confluent HUVEC monolayers on Transwells® were incubated with anti-αvβ3 and control antibodies (Ab) (10 µg/ml) 1 hour before stimulation with VEGF (30 ng/ml), TGF-β (10 ng/ml), or thrombin (10 U/ml). Data shown are the means+/−standard errors, n=3 for each group. Control vs. anti-αvβ3 Ab: p=0.972 for saline, p=0.033 for VEGF, p=0.041 for thrombin, p=0.029 for TGF-13.
FIG. 3E: β3 k.o. mice exhibit hemoconcentration after intraperitoneal injection of LPS (10 mg/kg). 36 hours after i.p. administration of LPS to β3 k.o. and wildtype control mice, blood was drawn via inferior venal caval puncture hematocrit levels measured. Data shown are the means+/−standard errors, n=6 for each group

Example 7: β3 k.o. Mice have Increased Mortality in i.p. LPS-Induced Sepsis Compared to Wild Type Controls We sought to determine if loss of αvβ3 function would enhance the hyperpermeable endothelial response in models of systemic sepsis. In an i.p. LPS-induced model of peritoneal sepsis, we found that β3 k.o. mice had increased mortality compared to wild type controls (FIG. 3A).

Example 8: β3 k.o. Mice have Local Extravasation of a FITC-BSA Tracer Around Mesenteric Vessels after i.p. Injection of LPS To determine if with the increased LPS-induced mortality in β3 deficiency is associated with increased systemic vascular permeability, we injected a FITC-BSA vascular tracer two hours prior to harvesting intact small bowel and mesentery for whole mount imaging. Intact vessels highlighted by FITC fluorescent were observed by microscopy. We found that β3 k.o. mice had increases in local mesenteric vessel tracer extravasation compared to WT controls after i.p. LPS administration (10 mg/kg) (FIG. 3B).

Example 9: β3 k.o. Mice have Increased $^{125}$I-BSA Extravasation into the Small Intestine/Mesentery and Colon after i.p. Injection of LPS (10 mg/kg)

To quantify this hyperpermeable response, we injected a $^{125}$I-BSA intravascular tracer two hours prior to harvesting mesentery/small bowel and colon en bloc. Whole organs were analyzed for total counts per minute (CPM) and normalized to serum counts. We found that there was a significant increase in $^{125}$I-BSA tracer in both mesentery/small bowel and colon in β3 k.o. compared to WT mice (FIG. 3C).

Example 10: Agonist-Induced Permeability in Human Umbilical Vein Endothelial Cells (HUVECs) is Enhanced by Antibody Inhibition of αvβ3

To determine if an endothelial hyperpermeable response with αvβ3 blockade would be relevant in endothelial cells derived from systemic blood vessels, we pretreated HUVECs with αvβ3 blocking antibodies and studied their effects on edemagenic agonist-induced permeability. Endothelial permeability was determined by measuring $C^{14}$-BSA flux across confluent monolayers grown on Transwells. We found that, as in HPAECs, Δvβ3-inhibiting antibodies enhanced the increased permeability response to VEGF, TGF-β, and thrombin in HUVECs (FIG. 3D).

Example 11: (33 k.o Mice Exhibit Hemoconcentration after i.p. LPS

The integrin β3 subunit (CD61) associates with both αv (CD51) and with αIIb (CD41) subunits. αII bβ3 is the major integrin on platelets and regulates platelet activation, aggregation, and function. To address the confounder of platelet dysfunction and possible hemorrhage, we measured the effect of i.p. LPS administration (10 mg/kg) on hematocrit. We found that the β3 k.o. mice had significant increases in hematocrit, providing evidence against significant hemorrhage, and rather, for an increase of vascular permeability and extravasation of plasma (FIG. 3E).

Figure 4:
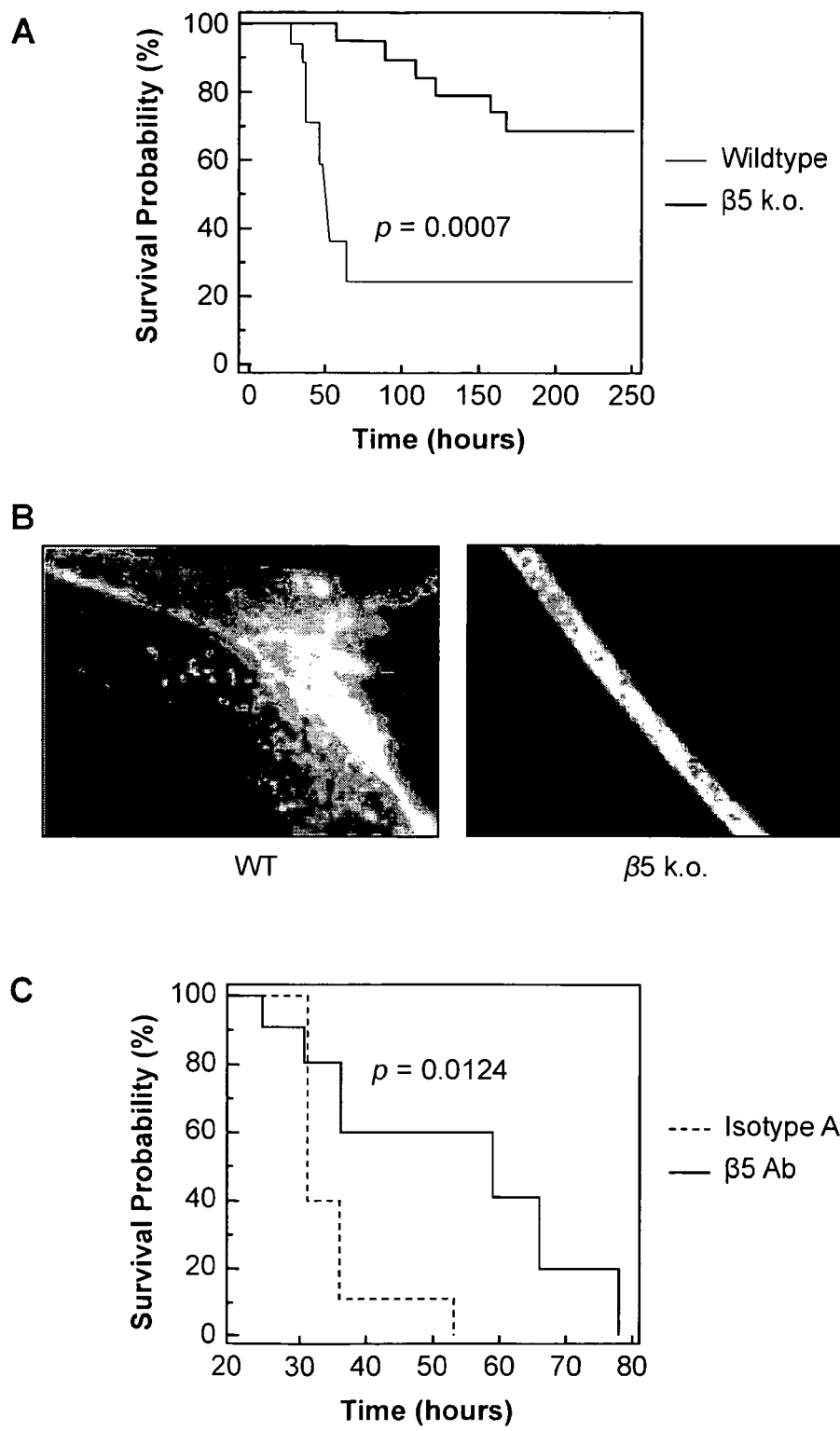
FIG. 4A: β5 k.o. mice have reduced mortality in an intraperitoneal LPS models of sepsis (13 mg/kg). Weight and sex-matched β5 k.o. and wildtype control mice were administered 13 mg/kg of LPS by i.p. injection. Data analyzed by Kaplan-Meier survival analysis, logrank test difference between groups, p=0.0007.
FIG. 4B: β5 k.o. mice decreased extravasation of a FITC-BSA tracer around mesenteric vessels after intraperitoneal injection of LPS (13 mg/kg) compared to wildtype controls. Sites of endothelial leakage were identified microscopically by using the FTIC-labeled BSA (90 micron size Sigma), which was injected retroorbitally (30 mg/kg in saline) one hour before the mouse was euthanized. Mesentery and small bowel was harvested en bloc taking care not to disrupt vasculature. Mesenteric whole mounts were prepared and fixed (Baluk et al. (1999) *Br J Pharmacol* 126:522). Sites of leakage were identified as areas of local FITC extravasation using a Leica DM5000B microscope.
FIG. 4C: Administration of αvβ5 blocking antibodies increases time to mortality in LPS-induced sepsis (13 mg/kg) compared to wildtype controls. Weight and sex-matched wildtype mice were administered 13 mg/kg of LPS by i.p. injection. 24 hours after LPS injection, the mice were randomized to retroorbital injection of either αvβ5 or isotype control antibodies. Data analyzed by Kaplan-Meier survival analysis, logrank test difference between groups, p=0.0124.

Example 12: β5 k.o. Mice have Increased Survival in an i.p. LPS Models of Sepsis αvβ5 blockade and deficiency confers protection against agonist-induced permeability. Our current studies show that αvβ5 and αvβ3 have opposite regulatory effects on vascular permeability, and that β3 k.o. mice have increased vascular permeability and mortality in LPS-induced sepsis. In the i.p. LPS-induced peritoneal sepsis model, we found that β5 k.o. mice had increased survival compared to wildtype controls (FIG. 4A). The result demonstrates that αvβ5 deficiency reduces vascular permeability and associated detrimental effects of sepsis.

Example 13: β5 k.o. Mice have Decreased Local Extravasation of a FITC-BSA Tracer Around Mesenteric Vessels after i.p. Injection of LPS To determine if a barrier-protective response occurs with β5 deficiency with i.p. LPS, we injected a FITC-BSA vascular tracer two hours prior to harvesting intact small bowel and mesentery for whole mount imaging. Intact vessels highlighted by FITC fluorescence were observed by microscopy. We found that β5 k.o. mice had decreased local mesenteric vessel tracer extravasation compared to wild type controls after i.p. LPS administration (13 mg/kg) (FIG. 4B).

Example 14: Administration of αvβ5 Blocking Antibodies Increases Time to Mortality in i.p. LPS-Induced Sepsis Compared to Wild Type Controls Twenty-four hours after administering i.p. LPS (13 mg/kg), wild type mice are morbidly ill, analogous to critically ill patients who are diagnosed with sepsis syndrome. At this point, the mice were treated with αvβ5 blocking vs. isotype control antibodies. We found that mice treated with αvβ5 blocking antibodies had a significant increased in time to mortality compared to mice treated with isotype controls (FIG. 4C).

These results are striking because the administration of αvβ5 blocking antibodies actually reverses sepsis. Usually, the acute nature of the septic reaction requires immediate intensive medical intervention, e.g., ventilation, dialysis, intravenous fluids, and antibiotics.

Example 15: Administration of αvβ5 Blocking Antibodies Increases Time to Mortality in Cecal Ligation and Puncture (CLP) Model for Sepsis Compared to Wild Type Controls To further investigate the ability of αvβ5 blocking antibodies to reverse sepsis, we performed a cecal ligation and puncture surgery, followed by administration of the ALULA αvβ5 antibody and a control (C7) antibody. CLP is a standard rodent model used to study polymicrobial peritoneal sepsis (see, e.g., Rittirsch et al. (2009) Nat. Protocols 4:31-36). In brief, the surgery involves ligation of the cecum at 50% distance between the tip of the ceum and the ileocecal valve followed by through-and-through puncture of the distal cecum with a 23 gauge needle. A small bead of stool (endogenous source of multiple bacterial species) is expressed through the puncture site. Perforation of the cecum results in bacterial peritonitis, followed by systemic activation of the inflammatory response and sepsis, and, finally, death.

Figure 5:
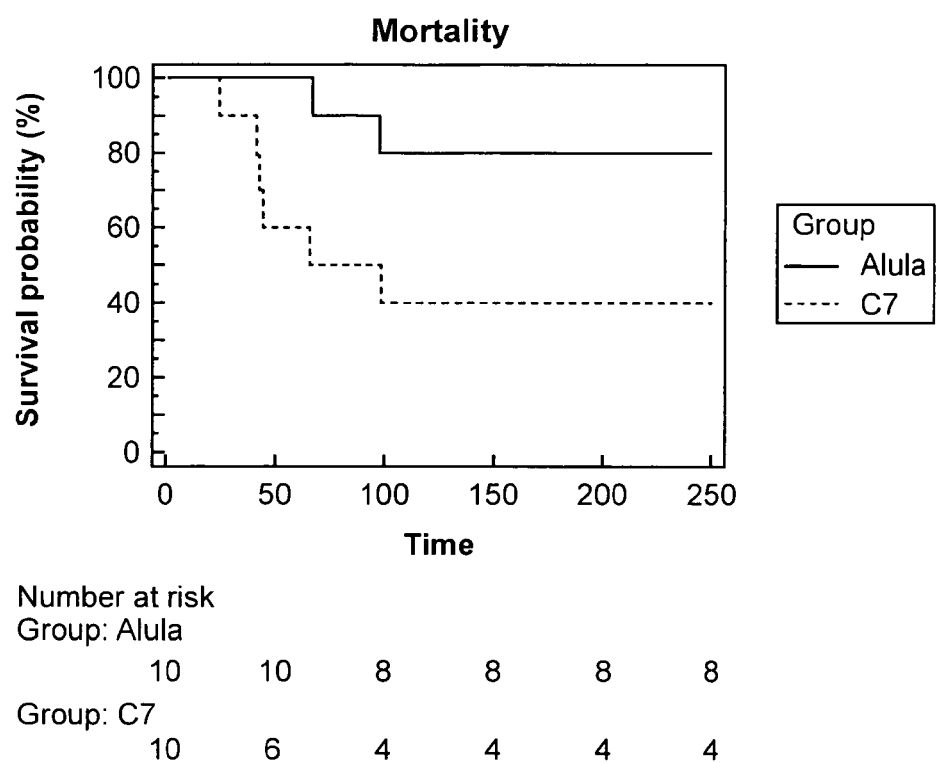
FIG. 5: Administration of αvβ5 blocking antibodies increases time to mortality in cecal ligation and puncture (CLP) induced sepsis compared to control. Weight and sex-matched wild type mice were subjected to CLP surgery. After surgery and closure of the abdominal incision, the mice were randomized to retroorbital injection of either αvβ5 or isotype control antibodies. Data analyzed by Kaplan-Meier survival analysis, logrank test difference between groups, p=0.0427.

We performed CLP surgery in 20 mice, with 10 each randomized to treatment with control antibody or αvβ5 antibody. After the CLP surgery was performed and the abdominal incision closed, αvβ5 or control antibodies were administered intravenously (iv) in one dose through a retroorbital plexus injection. Mortality was recorded as shown in FIG. 5 (time is in hours).

The results confirmed those from the LPS example. Again, administration of a αvβ5 blocking antibody significantly improved survival, with 80% of the mice surviving more than 10 days. In contrast, only 40% of the mice treated with control antibodies survived. Thus, administration of the αvβ5 blocking antibody after exposure to the bacterial infection was sufficient to reduce the likelihood of sepsis and death.

The above examples are provided to illustrate the invention but not to limit its scope. Other variants of the invention will be readily apparent to one of ordinary skill in the art and are encompassed by the appended claims. All publications, databases, patents, patent applications, and accession nos. cited herein are hereby incorporated by reference in their entirety for all purposes.

What is claimed is:

1. A method of treating severe sepsis in a human subject in need thereof, the method comprising administering to the human subject a therapeutically effective amount of an antibody specific for αvβ5 integrin, wherein said antibody specifically inhibits ligand binding to αvβ5 integrin and does not significantly bind to at least one of αvβ3, β3, αvβ6, β6, αvβ8 and β8 and wherein the antibody comprises the complementarity determining regions of the ALULA antibody produced by the hybridoma of ATCC Deposit No. PTA-5817.

2. The method of claim 1, wherein the antibody does not significantly bind to any of αvβ3, β3, αvβ6, β6, αvβ8 or β8.

3. The method of claim 1, wherein the antibody is a chimeric or a humanized antibody.

4. The method of claim 1, wherein the ligand is selected from the group consisting of vitronectin, fibronectin, osteopontin, tenascin c, and adenovirus penton base.

5. The method of claim 1, wherein the antibody is a humanized or chimeric ALULA.

6. The method of claim 1, wherein the administration is intraperitoneal or intravenous.

7. A method of treating septic shock in a human subject in need thereof, the method comprising administering to the human subject a therapeutically effective amount of an antibody specific for αvβ5 integrin, wherein said antibody specifically inhibits ligand binding to αvβ5 integrin and does not significantly bind to at least one of αvβ3, β3, αvβ6, β6, αvβ8 and β8 and wherein the antibody comprises the complementarity determining regions of the ALULA antibody produced by the hybridoma of ATCC Deposit No. PTA-5817.

8. The method of claim 7, wherein the antibody does not significantly bind to any of αvβ3, β3, αvβ6, β6, αvβ8 or β8.

9. The method of claim 7, wherein the antibody is a chimeric or a humanized antibody.

10. The method of claim 7, wherein the ligand is selected from the group consisting of vitronectin, fibronectin, osteopontin, tenascin c, and adenovirus penton base.

11. The method of claim 7, wherein the antibody is a humanized or chimeric ALULA.

12. The method of claim 7, wherein the administration is intraperitoneal or intravenous.

\* \* \* \* \*